(12) United States Patent
Ogawa et al.

(10) Patent No.: US 7,026,318 B2
(45) Date of Patent: Apr. 11, 2006

(54) COMPOUNDS EXHIBITING X-TYPE SPLA$_2$ INHIBITING EFFECT

(75) Inventors: Tomoyuki Ogawa, Osaka (JP); Kaoru Seno, Osaka (JP); Kohji Hanasaki, Osaka (JP); Minoru Ikeda, Osaka (JP); Takashi Ono, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 300 days.

(21) Appl. No.: 10/311,282

(22) PCT Filed: Jun. 27, 2001

(86) PCT No.: PCT/JP01/05479

§ 371 (c)(1),
(2), (4) Date: Dec. 17, 2002

(87) PCT Pub. No.: WO02/00621

PCT Pub. Date: Jan. 3, 2002

(65) Prior Publication Data

US 2003/0181454 A1 Sep. 25, 2003

(30) Foreign Application Priority Data

Jun. 29, 2000 (JP) .............................. 2000-195430

(51) Int. Cl.
| | | |
|---|---|---|
| A01N 43/58 | (2006.01) | |
| A01N 43/60 | (2006.01) | |
| A61K 31/495 | (2006.01) | |
| A61K 31/50 | (2006.01) | |
| C07D 241/36 | (2006.01) | |

(52) U.S. Cl. ....................................... 514/249; 544/349
(58) Field of Classification Search ................ 514/249; 544/349
See application file for complete search history.

(56) References Cited

FOREIGN PATENT DOCUMENTS

| CA | 2 346 334 | * 4/2000 |
|---|---|---|
| EP | 0 620 214 | 10/1994 |
| EP | 0 620 215 | 10/1994 |
| EP | 0 675 110 | 10/1995 |
| EP | 0 987 250 | 3/2000 |
| EP | 1 085 021 | 3/2001 |
| EP | 1 157 704 | 11/2001 |
| WO | 96/03120 | 2/1996 |
| WO | 96/03376 | 2/1996 |
| WO | 96/03383 | 2/1996 |
| WO | 97/21664 | 6/1997 |
| WO | 97/21716 | 6/1997 |
| WO | 98/18464 | 5/1998 |
| WO | 98/24437 | 6/1998 |
| WO | 98/24756 | 6/1998 |
| WO | 98/24794 | 6/1998 |
| WO | 98/25609 | 6/1998 |
| WO | 98/37069 | 8/1998 |
| WO | 99/09978 | 3/1999 |
| WO | 99/16453 | 4/1999 |
| WO | 99/25339 | 5/1999 |
| WO | 99/51605 | 10/1999 |
| WO | 99/57100 | 11/1999 |
| WO | 00/00201 | 1/2000 |
| WO | 00/21563 | 4/2000 |
| WO | 01/26653 | 4/2001 |

OTHER PUBLICATIONS

Blanchard et al, "Discovery of Bioavailable Inhibitors of Secretory Phospholipase A2" Pharmaceutical Biotechnology, vol. 11, pp. 445-463 (1998).*

Al-Dabbagh and Smith, "Species differences in oxidative drug metabolism: some basic considerations." Archives of toxicology. Supplement. Archiv fur Toxikologie. supplement, vol. 7, pp. 219-231 (1984).*

Hans Bundgaard, Design of Prodrugs, p. 1. © 1985 Elsevier Science Publishers.*

(Continued)

*Primary Examiner*—Zachary C. Tucker
(74) *Attorney, Agent, or Firm*—Wenderoth, Lind & Ponack, L.L.P.

(57) ABSTRACT

A compound represented by the general formula:

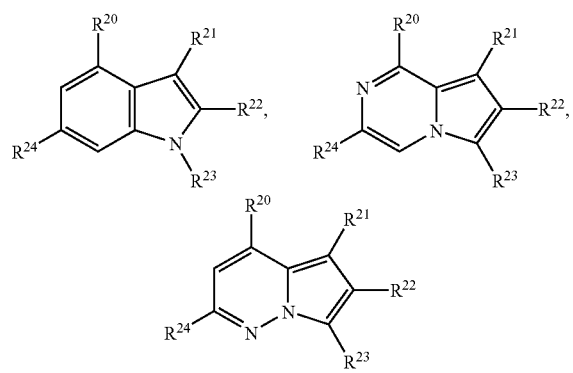

wherein $R^{20}$ is —CH$_2$COOH and the like; $R^{21}$ is —COCONH$_2$ and the like; $R^{22}$ is C4–C6 alkyl; and the like; $R^{23}$ is —CH$_2$—R$^{18}$ wherein $R^{18}$ is aryl and the like; $R^{24}$ is hydrogen or C1–C6 alkyl and the like; an optical active compound, a prodrug thereof, or a pharmaceutically acceptable salt, or a solvate having type X sPLA$_2$ inhibitory effect was found.

15 Claims, No Drawings

OTHER PUBLICATIONS

Richard B. Silverman, The Organic Chemistry of Drug Design and Drug Action, pp. 352-400. © 1992 Academic Press, Inc.*

Vippagunta et al, "Crystalline Solids" Advanced Drug Delivery Reviews, vol. 48, pp. 3-26 (2001).*

Gavezzotti, "Are Crystal Structures Predictable?" Accounts of Chemical Research, vol. 27, pp. 309-314 (1994).*

S. Hagishita et al., "Potent Inhibitors of Secretory Phospholipase A2: Synthesis and Inhibitory Activities of Indolizine and Indene Derivatives", J. Med. Chem., vol. 39, pp. 3636-3658, 1996.

K. Watanabe et al., "Role of the Prostaglandin E Receptor Subtype $EP_1$ in Colon Carcinogenesis[1]", Cancer Research, vol. 59, pp. 5093-5096, 1999.

* cited by examiner

COMPOUNDS EXHIBITING X-TYPE SPLA$_2$ INHIBITING EFFECT

This application is a U.S. national stage of International Application No. PCT/JP01/05479 filed Jun. 27, 2001.

1. Technical Field

The present invention relates to compounds exhibiting type X sPLA$_2$ inhibiting effect.

2. Background Art

As sPLA$_2$ inhibitors are known compounds described in EP-620214 (JP Laid-Open No. 95/010838, U.S. Pat. No. 5,578,634), EP-620215 (JP Laid-Open No. 95/025850, U.S. Pat. No. 5,684,034), EP-675110 (JP Laid-Open No. 95/285933, U.S. Pat. No. 5,654,326), WO 96/03120 (JP Laid-Open No. 98/505336), WO 96/03376 (JP Laid-Open No. 98/503208, U.S. Pat. No. 5,641,800), WO 96/03383 (JP Laid-Open No. 98/505584), WO 97/21664 (EP-779271), WO 97/21716 (EP-779273), WO 98/18464 (EP839806), WO 98/24437(EP846687), WO 98/24756, WO 98/24794, WO 98/25609, WO 99/51605, WO 99/59999 and the like, or parabromophenacylbromide, mepacrine, manoalide, theilocin A$_1$ and the like. However, these inhibitors have not been reported to have type X sPLA$_2$ inhibitory activities.

DISCLOSURE OF INVENTION

The present invention provides compounds exhibiting type X sPLA$_2$ inhibiting effect.

The inventors also examined the expression of type X sPLA$_2$ in various kinds of human pathological tissues with rabbit anti-human type X sPLA$_2$ polyclonal antibody. They found the elevated expression of type X sPLA$_2$ in several tumor tissues, hepatocytes of psudolobules of liver prepared from patients of liver cirrhosis, and some neuronal regions (senile plaques and neurofibrillary tangles) in brain tissues from patients of Alzheimer's disease.

The immunohistochemical analysis of each tissue was performed as follows. At first, anti-human type X sPLA$_2$ antibody was added to the slides prepared from normal adult tissues or tumor tissues from cancer patients and incubated for several hours. Next, in order to examine the expression of type X sPLA$_2$ in the tissues, the expression of type X sPLA$_2$ was visualized by using the methods such as the immunohistochemical labeling to detect the type X sPLA$_2$ signals. Consequently, the type X sPLA$_2$ signals were detected in the slides prepared from tumor tissues, suggesting that the expression of type X sPLA$_2$ is elevated in tumor tissues.

In addition, the inventors performed the experiments for neutralization of type X sPLA$_2$ signals. Precisely, before the addition of anti-human type X sPLA$_2$ antibody to the slides, the slides were incubated with the purified type X sPLA$_2$ protein for several hours. Hereafter, the slides were processed as the same procedures as described above to examine the type X sPLA$_2$ signals. Consequently, the type X sPLA$_2$ signals were disappeared in the slides prepared from tumor tissues.

Thus, the elevated expression of type X sPLA$_2$ was confirmed in human tumor tissues. According to the same procedures, the elevated expression of type X sPLA$_2$ was confirmed in the hepatocytes of psudolobules of liver prepared from patients of liver cirrhosis and some neuronal regions (senile plaques and neurofibrillary tangles) in brain tissues from patients of Alzheimer's disease.

In addition, the inventors examined the inhibitory effects of sPLA$_2$ inhibitors on the type X sPLA$_2$-induced release of oleic acid from tumor cells. Consequently, they confirmed that sPLA$_2$ inhibitors significantly blocked the type X sPLA$_2$-induced release of oleic acid from tumor cells.

On the other hand, potential involvement of PGE$_2$ in the development of tumors has been described in Cancer Research 59, 5093–5096, 1999. Then, the inventors examined the inhibitory effects of sPLA$_2$ inhibitors on the type X sPLA$_2$-induced PGE$_2$ production in tumor cells. Consequently, they confirmed that sPLA$_2$ inhibitors significantly blocked the type X sPLA$_2$-induced PGE$_2$ production in tumor cells.

Furthermore, the inventors examined the inhibitory effects of sPLA$_2$ inhibitors on the type X sPLA$_2$-induced release of fatty acids from isolated human lipoproteins. Consequently, they confirmed that sPLA$_2$ inhibitors significantly blocked the type sPLA$_2$-X-induced release of fatty acids from isolated human lipoproteins.

The inventors of the present invention accomplished the present invention as follows.

The present invention relates to I) a compound of the general formula (1):

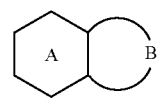

(I)

wherein A ring is a ring represented by the formula (a) to (c):

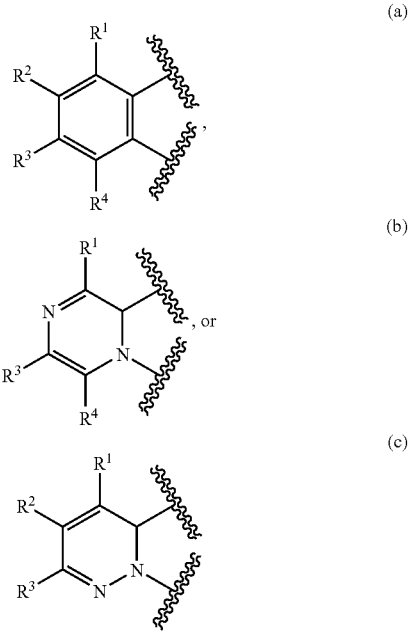

wherein R$^1$ and R$^2$ are each independently selected from hydrogen atom, non-interfering substituents, or —(L$^1$)-(acidic group) wherein L$^1$ is an acid linker having an acid linker length of 1 to 5, provided that at least one of the R$^1$ and R$^2$ is —(L$^1$)-(acidic group);

R$^3$ and R$^4$ are each independently selected from hydrogen atom, non-interfering substituents, carbocyclic groups, carbocyclic groups substituted with a non-interfering substituent(s), heterocyclic groups, or heterocyclic groups substituted with a non-interfering substituent(s);

—B— is represented by the formula (d) to (e):

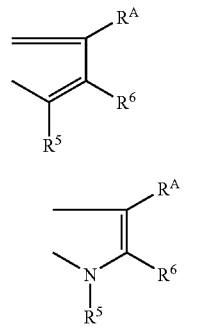

wherein $R^5$ is (f) C1–C20 alkyl, C2–C20 alkenyl, C2–C20 alkynyl, a carbocyclic group, or a heterocyclic group, (g) the groups represented by (f) each substituted independently with at least one group selected from non-interfering substituents, or —$(L^2)$—$R^8$ wherein $L^2$ is a divalent linking group of 1 to 18 atom(s) selected from hydrogen atom(s), nitrogen atom(s), carbon atom(s), oxygen atom(s), and sulfur atom(s), and $R^8$ is a group selected from the groups (f) and (g);

$R^6$ is optionally substituted C4–C8 alkyl, C3–C8 cycloalkyl C1–C4 alkyl, or aryl C1–C4 alkyl;

$R^4$ is represented by the formula:

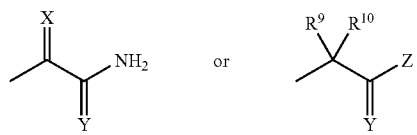

wherein $R^9$ and $R^{10}$ are each independently hydrogen atom, C1–C3 alkyl, or halogen;

X and Y are each independently oxygen atom or sulfur atom; and

Z is —$NH_2$ or —$NHNH_2$;

provided that —B— is (e), when A ring is (a);

a prodrug, a pharmaceutically acceptable salt, or a solvate thereof.

In more detail, the present invention relates to the following II) to XVII).

II) A compound of I) wherein $R^1$ is hydrogen atom or —$(L^3)$—$R^{11}$ wherein $L^3$ is —$OCH_2$—, —$SCH_2$—, —NH—$CH_2$—, —$CH_2CH_2$—, —O—$CH(CH_3)$—, or —O—CH$(CH_2CH_2C_6H_5)$—, $R^{11}$ is represented by the formula:

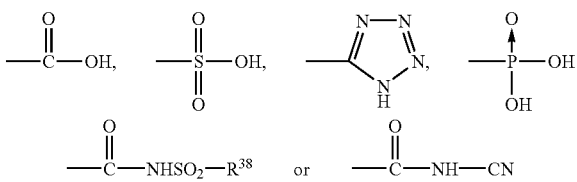

wherein $R^{38}$ is C1–C6 alkyl, C1–C3 haloalkyl, or aryl optionally substituted with C1–C6 alkyl, halogen, optionally substituted amino or nitro;

$R^2$ is hydrogen atom or —$(L^4)$—$R^{12}$ wherein $L^4$ is represented by the formula:

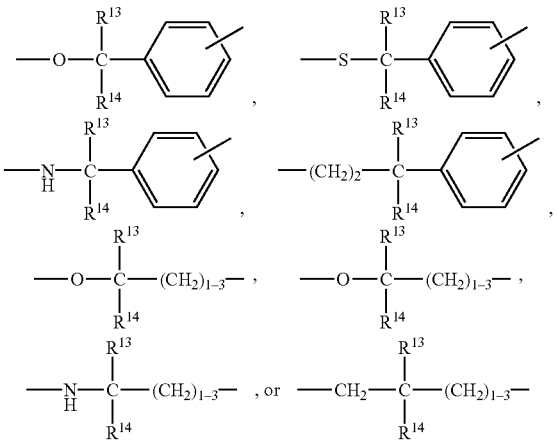

wherein $R^{13}$ and $R^{14}$ are each independently hydrogen atom, C1–C10 alkyl, C1–C10 aralkyl, carboxy, alkyloxycarbonyl, or halogen; $R^{12}$ is —COOH, —$SO_3H$, or —$P(O)(OH)_2$;

provided that $R^1$ and $R^2$ are not hydrogen atoms at the same time;

a prodrug, a pharmaceutically acceptable salt, or a solvate thereof.

III) A compound of I) or II) wherein $R^3$ is hydrogen atom, C1–C6 alkyl, C3–C6 cycloalkyl, aryl, or a heterocyclic group, and $R^4$ is hydrogen atom or halogen;

a prodrug, a pharmaceutically acceptable salt, or a solvate thereof.

IV) A compound of any one of I) to III) wherein $R^5$ is —$(CH_2)_{1-6}$—$R^{15}$ wherein $R^{15}$ is represented by the formula:

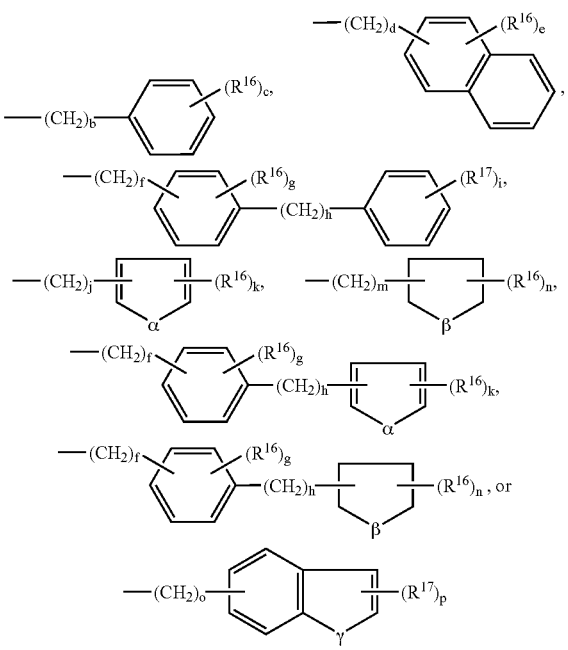

wherein b, d, f, h, j, m, and o are each independently an integer from 0 to 2, $R^{16}$ and $R^{17}$ are each independently halogen, C1–C10 alkyl, C1–C10 alkyloxy, C1–C10 alkylthio, aryloxy, or C1–C10 haloalkyl, α is oxygen atom or sulfur atom, β is —CH$_2$— or —(CH$_2$)$_2$—, γ is oxygen atom or sulfur atom, c, i, and p are each independently an integer from 0 to 5, e is an integer from 0 to 7, g is an integer from 0 to 4, k and n are each independently an integer from 0 to 3;

a prodrug, a pharmaceutically acceptable salt, or a solvate thereof.

V) A compound of IV) wherein $R^5$ is —CH$_2$—$R^{18}$ wherein $R^{18}$ is represented by the formula:

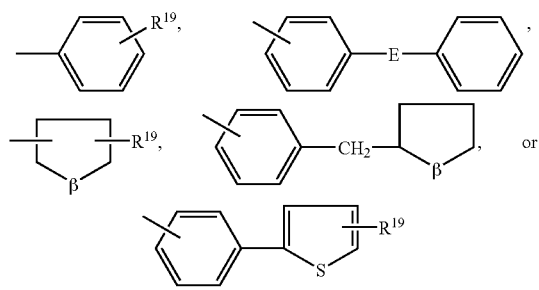

wherein β is —CH$_2$—, or —(CH$_2$)$_2$—; $R^{19}$ is hydrogen atom, C1–C3 alkyl or halogen; E is a bond, —CH$_2$—, or —O—;

a prodrug, a pharmaceutically acceptable salt, or a solvate thereof.

VI) A compound of any one of I) to V) wherein $R^1$ is —OCH$_2$COOH or —OCH$_2$CONHSO$_2$R$^{38}$ wherein $R^{38}$ is C1–C6 alkyl, C1 haloalkyl, or aryl;

a pharmaceutically acceptable salt, or a solvate thereof.

VII) A compound of any one of I) to VI) wherein $R^2$ is hydrogen atom;

a pharmaceutically acceptable salt, or a solvate thereof.

VIII) A compound of any one of I) to VII) wherein $R^6$ is C4–C6 alkyl;

a pharmaceutically acceptable salt, or a solvate thereof.

IX) A compound of any one of I) to VIII) wherein $R^4$ is —CH$_2$CONH$_2$ or —COCONH$_2$;

a pharmaceutically acceptable salt, or a solvate thereof.

X) A compound of the general formula (II):

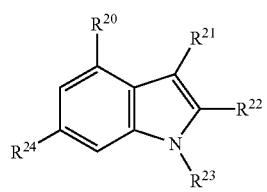

(II)

wherein $R^{20}$ is —OCH$_2$COOH, —OCH$_2$CONHSO$_2$CH$_3$, or —OCH$_2$CONHSO$_2$C$_6$H$_5$; $R^{21}$ is —COCONH$_2$, —CH$_2$CONH$_2$, or —CH$_2$CONHNH$_2$; $R^{22}$ is C4–C6 alkyl; $R^{23}$ is —CH$_2$—$R^{18}$ wherein $R^{18}$ is represented by the formula:

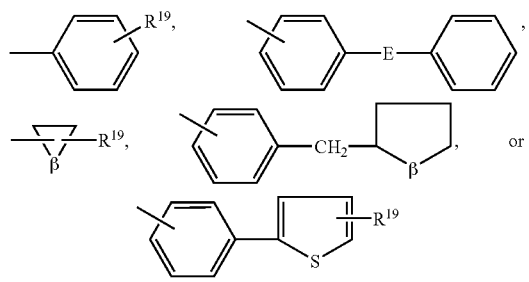

wherein β is —(CH$_2$)$_{1-6}$—; $R^{19}$ is hydrogen, C1–C3 alkyl, or halogen; E is a single bond, —CH$_2$—, or —O—; $R^{24}$ is hydrogen or C1–C6 alkyl;

a pharmaceutically acceptable salt, or a solvate thereof.

XI) A compound of the general formula (III):

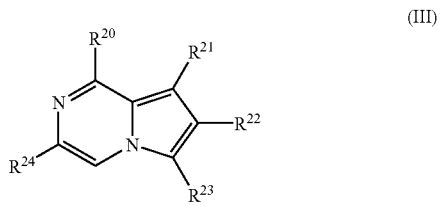

(III)

wherein $R^{20}$, $R^{21}$, $R^{22}$ $R^{23}$, and $R^{24}$ are as defined in X);

a pharmaceutically acceptable salt, or a solvate thereof.

XII) A compound of the general formula (IV):

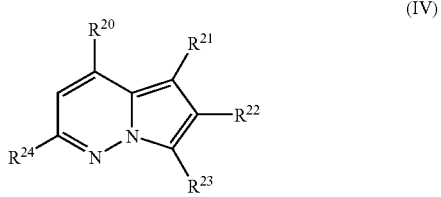

(IV)

wherein $R^{20}$, $R^{21}$, $R^{22}$, $R^{23}$, and $R^{24}$ are as defined in X);

a pharmaceutically acceptable salt, or a solvate thereof.

XIII) A pharmaceutical composition which contains as an active ingredient a compound of any one of I) to XII).

XIV) A type X sPLA$_2$ inhibitor which contains as an active ingredient a compound of any one of I) to XII).

XV) A preventing agent or treating agent for cancer, liver cirrhosis, Alzheimer's disease and/or arteriosclerosis which contains as an active ingredient a compound of any one of I) to XII).

XVI) Use of a compound of any one of I) to XII) for the preparation of medicament for treating cancer, liver cirrhosis, Alzheimer's disease and/or arteriosclerosis.

XVII) A method of treating a mammal for diminishing influence caused by cancer, liver cirrhosis, Alzheimer's disease and/or arteriosclerosis comprising administering to said mammal including human a therapeutically effective amount of a compound of any one of I) to XII).

The present invention is explained in detail as follows.

In the case where a compound represented by the general formula (I) to (IV) has one or more of chiral center(s), it may exist as an optically active member. Likewise, in the case where a compound contains alkenyl or alkenylene, there is a possibility of cis- and trans-isomers. Mixtures of R- and S-isomers as well as of cis- and trans-isomers, and mixtures of R- and S-isomers containing racemic mixture are included in the scope of the present invention. An asymmetric carbon atom may exist also in a substituent such as alkyl group. All such isomers and these mixtures are included in the present invention. In the case where a specified stereoisomer is desired, it is manufactured by applying a manner well known by those skilled in the art wherein a previously separated starting material having an asymmetrical center is subjected to stereospecific reaction, or it is manufactured by preparing a mixture of stereoisomers, and thereafter separating the mixture in accordance with a well-known manner.

Prodrug is a derivative of the compound represented by the general formula (I) to (IV) having a group which can be decomposed chemically or metabolically, and such prodrug is a compound which becomes pharmaceutically active by means of solvolysis or by placing the compound in vivo under a physiological condition. Although a derivative of the compounds exhibits activity in both forms of acid derivative and basic derivative, acid derivative is more advantageous in solubility, tissue affinity, and release control in mammal organism (Bungard, H., Design of Prodrugs, pp. 7–9, 21–24, Elsevier, Amsterdam, 1985). For instance, prodrugs each containing an acid derivative such as an ester which is prepared by reacting a basal acid compound with a suitable alcohol, or an amide which is prepared by reacting a basal acid compound with a suitable amine are well known by those skilled in the art. Aliphatic or aromatic esters derived from acid groups contained in the compounds according to the present invention are preferable prodrugs. Particularly preferred esters as prodrugs are C1–C6 alkylester (e.g. methyl ester, ethyl ester). Double ester such as (acyloxy)alkyl ester or ((alkyloxycarbonyl)oxy)alkyl ester type prodrugs may be optionally manufactured.

Where a compound represented by the general formula (I) to (IV) has an acidic or basic functional group, a variety of salts having higher water solubility and more physiologically suitable properties than those of the original compound can be formed. An example of typical pharmaceutically acceptable salts includes salts with alkali metal and alkaline earth metal such as lithium, sodium, potassium, magnesium, aluminum and the like, but it is to be noted that such pharmaceutically acceptable salts are not limited thereto. A salt is easily manufactured from a free acid by either treating an acid in a solution with a base, or allowing an acid to be in contact with an ion exchange resin. Addition salts of the compounds represented by the general formula (I) to (IV) with relatively non-toxic inorganic bases and organic bases, for example, amine cation, ammonium, and quaternary ammonium derived from nitrogenous bases having a basicity sufficient for forming a salt of the compounds of the present invention are included in the definition of "pharmaceutically acceptable salts". (e.g., S. M. Berge et al., "Pharmaceutical Salts," J. Phar. Sci., 66, 1–19 (1977)). Furthermore, basic groups of a compound represented by the general formula (I) to (IV) having sPLA$_2$ inhibitory activities are reacted with a suitable organic or inorganic acid to form salts such as acetates, benzenesulfonates, benzoates, bicarbonates, bisulfates, bitartarate, borates, bromides, camcyrates, carbonates, chlorides, clubranates, citrates, edetates, edicirates, estrates, ethylates, fluorides, fumarates, glusep- tates, gluconates, glutamates, glycolialsanyrates, hexylresorcinates, hydroxynaphthoates, iodides, isothionates, lactates, lactobionates, laurates, malates, malseates, manderates, mesylates, methylbromides, methylnitrates, methylsulfates, mucates, napcylates, nitrates, oleates, oxarates, palmitates, pantothenates, phosphates, polygalacturonates, salicirates, stearates, subacetates, sucinates, tanates, tartrates, tosylates, trifluoroacetates, trifluoromethanesulfonates, valerates and the like.

The solvate includes solvates with organic solvents and/or hydrates. In case of forming a hydrate, a questioned compound may be coordinated with a suitable number of water molecules.

The term "pharmaceutically acceptable" means that it is not harmful for recipients.

The cancer means malignant tumors originated from epithehal cells in various tissues, cells such as colon cancer, lung cancer, liver cancer, stomach cancer, renal cancer, gallbladder cancer, prostate cancer, pancreatic cancer, testis cancer, ovarian cancer, skin cancer, esophageal cancer, laryngeal cancer, breast cancer and uterine cancer. Based on the experiments, the inventors confirmed the elevated expression of type X sPLA$_2$ in various tumor tissues, including colon adenocarcinoma, lung bronchiolalveolar carcinoma, liver nodulous hepatocellular carcinoma, stomach adenocarcinoma, renal granular cell carcinoma, gallbladder adenocarcinoma, neoplasia of prostate, pancreatic intradactual adenocarcinoma, testis embrionic carcinoma, ovarian adenocarcinoma or malignant melanoma originated from epithelium malignancy. Especially, the invention is useful for the prevention or treatment of colon cancer, lung cancer, liver cancer, stomach cancer, renal cancer, gallbladder cancer, prostate cancer, pancreatic cancer, testis cancer, ovarian cancer or skin cancer.

"Hepatocirrhosis" is a progressive hepatopathy which comprises wide suffer damage of liver parenchymal cell accompanied with reconstruct of hepatic lobule structure, causes often jaundie, portal hypeternsion, or hydroperitoneum, and finally hepatargy. Based on the experiments, the inventors confirmed the elevated expression of type X sPLA$_2$ in pseudoacinus of hepatocytes derived from patient of liver cirrhosis. Especially, the invention is useful for preventing or treating liver cirrhosis.

"Alzheimer's disease" is a progressive derangement assumed disturbance of memory or disturbance of orientation, being characteristic of dwarf of cerebrum, especially temporal lobe, on pathology, and change of neurofibril and senile plaque on histology. Based on the experiments, the inventors confirmed the elevated expression of type X sPLA$_2$ in some neurons in brain tissues from patients of Alzheimer's disease, especially in senile plaques and neurofibrillary tangles. In particular, the compounds in this invention are useful for preventing or treating Alzheimer's disease.

"Arteriosclerosis" is the general term of local arterial lesion which exhibits reduction of hyperplasy, reconstruct and resilience of arterial mural, and depression. On pathology arterial sclerosis is classified into three types, and among them the most important is arteriosclerosis which is a basis of critical disease such as coronary artery disease, brain infarction and aortic aneurysm. Based on the experiments, the inventors confirmed that the compounds in this invention significantly blocked the type X sPLA$_2$-induced release of fatty acids from human lipoproteins. Especially, these compounds are useful for preventing or treating arterial sclerosis.

In the present specification, the term "alkyl" employed alone or in combination with other terms means a straight- or branched chain monovalent hydrocarbon group having a specified number of carbon atoms. An example of the alkyl includes methyl, ethyl, n-propyl, isopropyl, n-butyl, isobutyl, sec-butyl, tert-butyl, n-pentyl, n-hexyl, isopentyl, neopentyl, tert-pentyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl and the like.

The term "alkenyl" employed alone or in combination with other terms in the present specification means a straight- or branched chain monovalent hydrocarbon group having a specified number of carbon atoms and at least one double bond. An example of the alkenyl includes vinyl, allyl, propenyl, crotonyl, isopentenyl, a variety of butenyl isomers and the like.

The term "alkynyl" used in the present specification means a straight or branched chain monovalent hydrocarbon group having a specified number of carbon atoms and at least one triple bond. The alkynyl may contain (a) double bond(s). An example of the alkynyl includes ethynyl, propynyl, 6-heptynyl, 7-octynyl, 8-nonynyl and the like.

The term "carbocyclic group" used in the present specification means a group derived from a saturated or unsaturated, substituted or unsubstituted 5 to 14 membered, preferably 5 to 10 membered, and more preferably 5 to 7 membered organic nucleus whose ring forming atoms other than hydrogen atoms are solely carbon atoms. A group containing two to three of the carbocyclic group is also included in the above stated group. An example of typical carbocyclic groups includes cycloalkyl such as cyclopropyl, cyclobutyl, cyclopentyl, cyclohexyl, cycloheptyl, and cyclooctyl, cycloalkenyl such as cyclobutylenyl, cyclopentenyl, cyclohexenyl, cycloheptenyl, and cyclooctenyl, phenyl, naphthyl, norbornyl, bicycloheptadienyl, indenyl, stilbenyl, terphenylyl, phenylcyclohexenyl, acenaphthyl, anthryl, biphenylyl, bibenzyl, and a phenylalkylphenyl derivative represented by the formula (V):

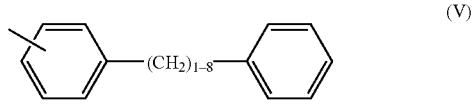

(V)

Phenyl, cycloalkyl or the like is preferred as a carbocyclic groups in $R^3$ and $R^4$.

The term "heterocyclic group" used in the present specification means a group derived from a monocyclic or polycyclic, saturated or unsaturated, substituted or unsubstituted heterocyclic nucleus having 5 to 14 ring atoms and containing 1 to 3 hetero atoms selected from the group consisting of nitrogen atom, oxygen atom, and sulfur atom. An example of the heterocyclic group includes pyridyl, pyrrolyl, furyl, benzofuryl, thienyl, benzothienyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo[1,2-a]pyridinyl, benzotriazolyl, anthranilyl, 1,2-benzisoxazolyl, benzoxazolyl, benzothiazolyl, purinyl, puridinyl, dipyridinyl, phenylpyridinyl, benzylpyridinyl, pyrimidinyl, phenylpyrimidinyl, pyrazinyl, 1,3,5-triazinyl, quinolyl, phthalazinyl, quinazolinyl, quinoxalinyl, and the like.

Furyl, thienyl or the like is preferred as a heterocyclic group in the $R^3$ and $R^4$.

In $R^5$, preferable carbocyclic and heterocyclic groups are represented by the formula:

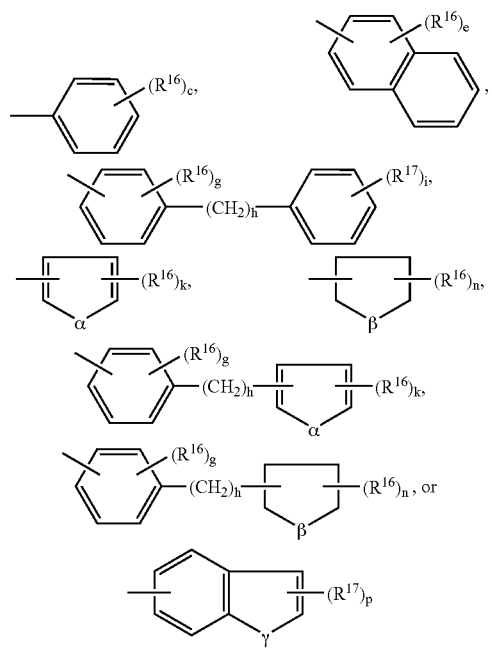

wherein h is an integer from 0 to 2, $R^{16}$ and $R^{17}$ are each independently halogen, C1–C10 alkyl, C1–C10 alkyloxy, C1–C10 alkylthio, aryloxy, or C1–C10 haloalkyl, α is oxygen atom or sulfur atom, β is —CH$_2$— or —(CH$_2$)$_2$—, γ is oxygen atom or sulfur atom, c, i, and p are each independently an integer from 0 to 5, e is an integer from 0 to 7, g is an integer from 0 to 4, k and n are each independently an integer from 0 to 3.

When the above c, e, f, g, i, k, n, and/or p are 2 or more, a plural number of $R^{16}$ or $R^{17}$ may be different from one another. When $R^{16}$ is a substituent on the naphthyl group, the substituent may be substituted at any arbitrary position on the naphthyl group. A more preferable example includes a group represented by the formula:

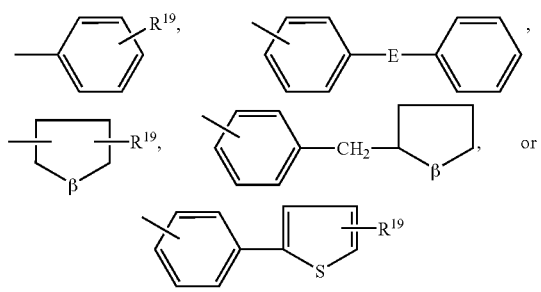

wherein β is —CH$_2$— or —(CH$_2$)$_2$—; $R^{19}$ is hydrogen atom, C1–C3 alkyl or halogen; E is a bond, —CH$_2$—, or —O—.

As $R^5$, preferred are the above mentioned carbocyclic C1–C3 alkyl and the above mentioned heterocyclic C1–C3 alkyl.

The term "non-interfering substituent" in the present specification means a group suitable for substitution of the above mentioned "carbocyclic group", "heterocyclic group", and basic skeleton. An example of the non-interfering substituents includes C1–C10 alkyl, C2–C6 alkenyl, C2–C6 alkynyl, C7–C12 aralkyl such as benzyl and phenethyl, C7–C12 alkaryl, C3–C8 cycloalkyl, phenyl, tolyl, xylyl, biphenylyl, C1–C10 alkyloxy, C1–C6 alkyloxy C1–C6 alkyl such as methyloxymethyl, ethyloxymethyl, methyloxyethyl, and ethyloxyethyl, C1–C6 alkyloxy C1–C6 alkyloxy such as methyloxymethyloxy and methyloxyethyloxy, C1–C6 alkylcarbonyl such as methylcarbonyl and ethylcarbonyl, C1–C6 alkylcarbonylamino such as methylcarbonylamino and ethylcarbonylamino, C1–C6 alkyloxyamino such as methyloxyamino and ethyloxyamino, C1–C6 alkyloxyaminocarbonyl such as methyloxyaminocarbonyl and ethyloxyaminocarbonyl, mono or di C1–C6 alkylamino such as methylamino, ethylamino, dimethylamino, and ethylmethylamino, C1–C10 alkylthio, C1–C6 alkylthiocarbonyl such as methylthiocarbonyl and ethylthiocarbonyl, C1–C6 alkylsulfinyl such as methylsulfinyl and ethylsulfinyl, C1–C6 alkylsulfonyl such as methylsulfonyl and ethylsulfonyl, C2–C6 haloalkyloxy such as 2-chloroethyloxy and 2-bromoethyloxy, C1–C8 haloalkylsulfonyl such as chloromethylsulfonyl and bromomethylsulfonyl, C1–C10 haloalkyl, C1–C6 hydroxyalkyl such as hydroxymethyl and hydroxyethyl, C1–C6 alkyloxycarbonyl such as methyloxycarbonyl and ethyloxycarbonyl, —(CH$_2$)$_{1-8}$—O—(C1–C6 alkyl), benzyloxy, aryloxy such as phenyloxy, arylthio such as phenylthio, —(CONHSO$_2$R$^{25}$) wherein R$^{25}$ is C1–C6 alkyl or aryl, —CHO, amino, amidino, halogen, carbamyl, carboxyl, carbalkoxy, —(CH$_2$)$_{1-8}$—COOH such as carboxymethyl, carboxyethyl, and carboxypropyl, cyano, cyanoguanidino, guanidino, hydrazide, hydrazino, hydroxy, hydroxyamino, nitro, phosphono, —SO$_3$H, thioacetal, thiocarbonyl, a carbocyclic group, a heterocyclic group and the like. These are optionally substituted with one or more substituents selected from the group consisting of C1–C6 alkyl, C1–C6 alkyloxy, C1–C6 haloalkyloxy, C2–C6 haloalkyl, and halogen.

Preferable are halogen, C1–C6 alkyl, C1–C6 alkyloxy, C1–C6 alkylthio, and C1–C6 haloalkyl as the "non-interfering substituent" of "substituted with non-interfering substituent" in R$^3$, R$^4$, and R$^5$. More preferable are halogen, C1–C3 alkyl, C1–C3 alkyloxy, C1–C3 alkylthio, and C1–C3 haloalkyl.

Preferable are C1–C6 alkyl, aralkyl, C1–C6 alkyloxy, C1–C6 alkylthio, C1–C6 hydroxyalkyl, C2–C6 haloalkyloxy, halogen, carboxy, C1–C6alkyloxycarbonyl, aryloxy, arylthio, a carbocyclic group, and a heterocyclic group as the "non-interfering substituent" in R$^1$, R$^2$, R$^3$, and R$^4$. More preferable are halogen, C1–C6 alkyl, aralkyl, carboxy, C1–C6 hydroxyalkyl, phenyl, and C1–C6 alkyloxycarbonyl.

The term "halogen" in the present specification means fluorine, chlorine, bromine, and iodine.

The term "cycloalkyl" in the present specification means a monovalent cyclic hydrocarbon group having a specified number of carbon atoms. An example of the cycloalkyl includes cyclopropyl, cyclobutyl, cyclopentyl, cyclohexyl, cycloheptyl, cyclooctyl and the like.

The term "cycloalkenyl" in the present specification means a monovalent cyclic hydrocarbon group having a specified number of carbon atoms and at least one double bond(s). An example of the cycloalkenyl includes 1-cyclopropenyl, 2-cyclopropenyl, 1-cyclobutenyl, 2-cyclobutenyl and the like.

In the present specification, an example of "alkyloxy" includes methyloxy, ethyloxy, n-propyloxy, isopropyloxy, n-butyloxy, n-pentyloxy, n-hexyloxy and the like.

In the present specification, an example of "alkylthio" includes methylthio, ethylthio, n-propylthio, isopropylthio, n-butylthio, n-pentylthio, n-hexylthio and the like.

The term "acidic group" in the present specification means an organic group functioning as a proton donor capable of hydrogen bonding when attached to a basic skeleton through a suitable linking atom (hereinafter defined as "acid linker"). An example of the acidic group includes a group represented by the formula:

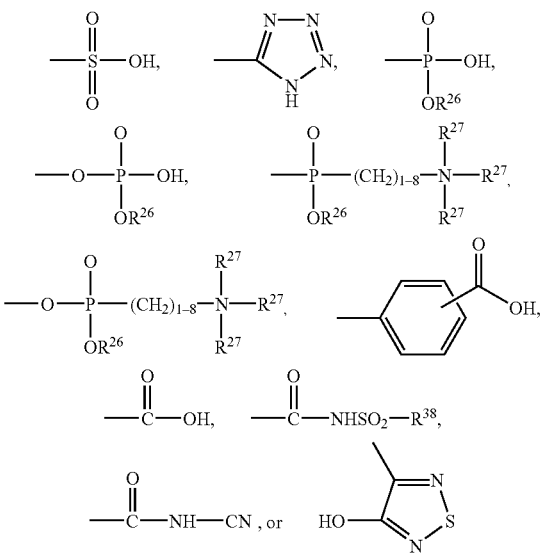

wherein R$^{26}$ is hydrogen atom, metal, or C1–C10 alkyl; R$^{27}$ is each dependently hydrogen atom or C1–C10 alkyl, R$^{38}$ is C1–C6 alkyl, C1–C3 haloalkyl, or C1–C6 alkyl, halogen, optionally substituted amino, or aryl optionally substituted with nitro; and provided that when acidic group having both of R$^{26}$ and R$^{27}$, at least one of R$^{26}$ and R$^{27}$ is hydrogen atom. As an acidic group are preferred —COOH, —SO$_3$H, P(O)(OH)$_2$, or —CONHSO$_2$R$^{38}$ wherein R$^{38}$ is C1–C6 alkyl, C1–C3 haloalkyl, or C1–C6 alkyl, halogen, optionally substituted amino, or aryl optionally substituted with nitro. As a more preferred acidic group is —CONHSO$_2$R$^{38}$ wherein R$^{38}$ is C1–C6 alkyl or aryl.

The term "acid linker" in the present specification means a divalent linking group represented by a symbol —(L$^1$)—, and it functions to join a basic skeleton to an "acidic group" in the general relationship. An example of it includes a group represented by the formula:

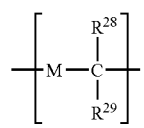

wherein M is —CH$_2$—, —O—, —N(R$^{30}$)—, or —S—; R$^{28}$ and R$^{29}$ are each independently hydrogen atom, C1–C10 alkyl, aryl, aralkyl, carboxy, or halogens, and a group represented by the formula:

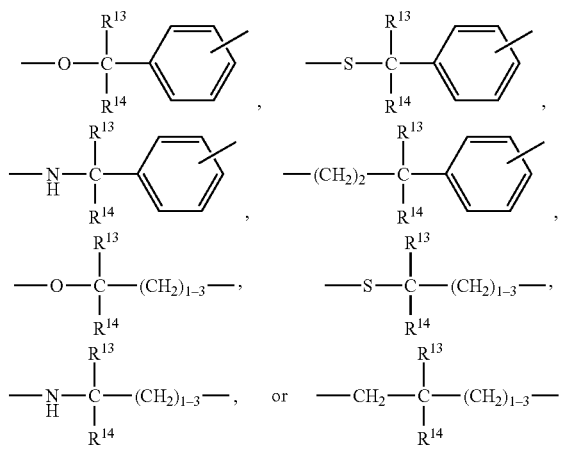

wherein $R^{13}$ and $R^{14}$ are each independently hydrogen atom, C1–C10 alkyl, C1–C10 aralkyl, carboxy, alkyloxycarbonyl, or halogen. Preferable are —O—CH$_2$—, —S—CH$_2$—, —N($R^{30}$)—CH$_2$—, —CH$_2$—CH$_2$—, —O—CH(CH$_3$)—, or —O—CH((CH$_2$)$_2$C$_6$H$_5$)— wherein $R^{30}$ C1–C6 alkyl. More preferable is —O—CH$_2$— or —S—CH$_2$—.

In the present specification, the term "acid linker length" means the number of atoms (except for hydrogen atoms) in the shortest chain of a linking group —(L$^1$)— which connects a basic skeleton with the "acidic group". The presence of a carbocyclic ring in —(L$^1$)— counts as the number of atoms approximately equivalent to the calculated diameter of the carbocyclic ring. Thus, a benzene and cyclohexane ring in the acid linker counts as two atoms in calculating the length of —(L$^1$)—. A preferable length is 2 to 3.

The term "haloalkyl" in the present specification means the aforementioned "alkyl" substituted with the aforementioned "halogen" at arbitrary position(s). An example of the haloalkyl includes chloromethyl, trifluoromethyl, 2-chloromethyl, 2-bromomethyl and the like.

The term "hydroxyalkyl" in the present specification means the aforementioned "alkyl" substituted with hydroxy at arbitrary position(s). An example of the hydroxyalkyl includes hydroxymethyl, 2-hydroxyethyl, 3-hydroxypropyl and the like. In this case, hydroxymethyl is preferable.

In the present specification, the term "haloalkyl" in "haloalkyloxy" is the same as defined above. An example of it includes 2-chloroethyloxy, 2-trifluoroethyloxy, 2-chloroethyloxy and the like.

The term "aryl" in the present specification means a monocyclic or condensed cyclic aromatic hydrocarbon. An example of the aryl includes phenyl, 1-naphthyl, 2-naphthyl, anthryl and the like. Particularly, phenyl and 1-naphthyl are preferred.

The term "aralkyl" in the present specification means a group wherein the aforementioned "alkyl" is substituted with the above-mentioned "aryl". Such aryl may have a bond at any substitutable position. An example of it includes benzyl, phenethyl, phenylpropyl such as 3-phenylpropyl, naphthylmethyl such as 1-naphthylmethyl and the like.

An example of the "alkyloxycarbonyl" in the present specification includes methyloxycarbonyl, ethyloxycarbonyl, n-propyloxycarbonyl and the like.

An example of the "aryloxy" in the present specification includes phenyloxy and the like.

An example of the "arylthio" in the present specification includes phenylthio and the like.

The term "halophenyl" in the present specification means phenyl substituted with the aforementioned "halogen" at one or more position(s). An example of the halophenyl includes fluorophenyl, chlorophenyl, bromophenyl, iodophenyl, difluorophenyl, dichlorophenyl, dibromophenyl, trifluorophenyl, trichlorophenyl, tribromophenyl, chlorofluorophenyl, bromochlorophenyl, and the like.

Preferable combinations of "A ring" and "—B—" are represented by the following (h)–(j):

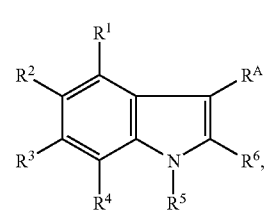

(h)

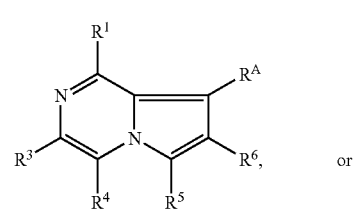

(i)

or

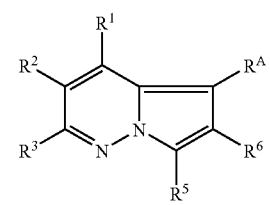

(j)

In compounds of (h) to (j), preferred are those wherein $R^1$ is —OCH$_2$COOH or —OCH$_2$CONHSO$_2$R$^{38}$ wherein $R^{38}$ is C1–C6 alkyl, C1 haloalkyl, or aryl, $R^2$ is hydrogen atom, $R^3$ is hydrogen atom or C1–C6 alkyl, $R^4$ is hydrogen atom, $R^5$ is —(CH$_2$)$_{1-2}$—$R^{18}$ wherein $R^{18}$ is represented by the formula:

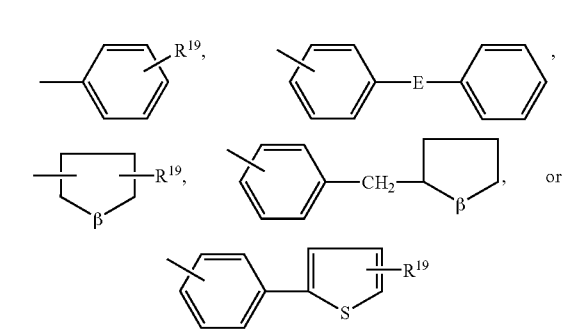

wherein β is —CH$_2$— or —(CH$_2$)$_2$—; $R^{19}$ is hydrogen atom, C1–C3 alkyl, or halogen; E is a single bond, —CH$_2$—, or —O—; $R^6$ is C4–C6 alkyl; $R^4$ is —COCONH$_2$.

BEST MODE FOR CARRYING OUT THE INVENTION

Compounds (I) to (IV) of the present invention can be prepared by the methods described in EP0675110 A1, WO 99/51605, WO 99/59999, and the like. The representative schema of indole derivatives, pyrro[1,2-a]pyrazine derivatives, and pyrro[1,2-b]pyrazine are shown as follows.

(Method A): Synthetic Method of Indole Derivatives (1)

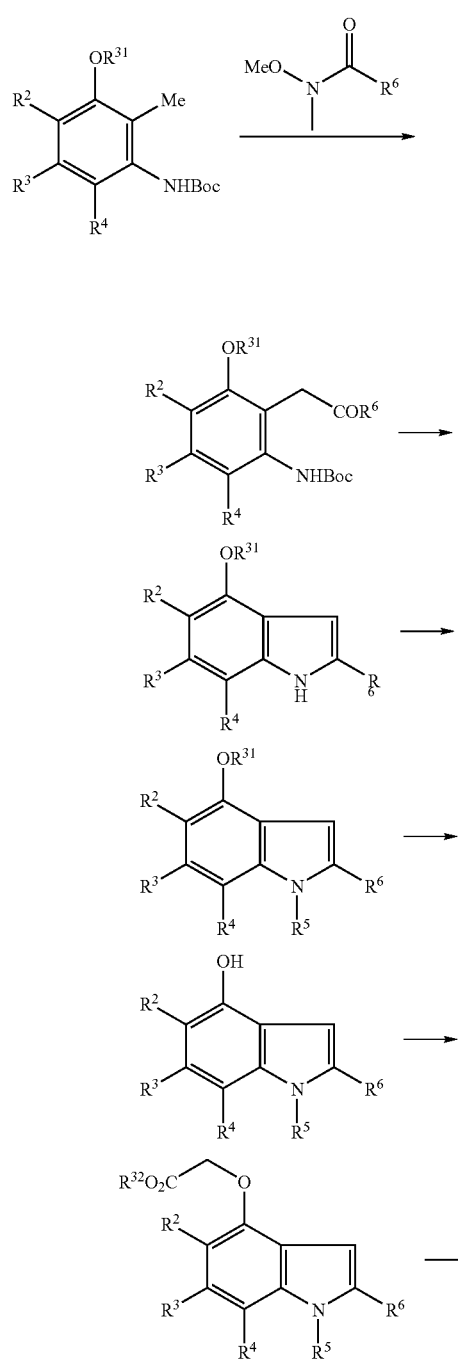

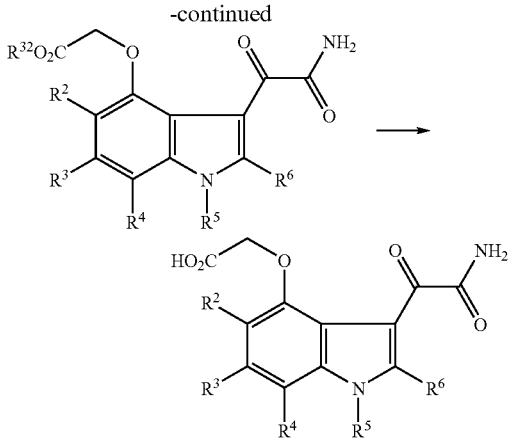

wherein $R^2$, $R^3$, $R^4$, $R^5$, and $R^6$ are as defined above; $R^{31}$ and $R^{32}$ are C1–C5 alkyl.

(Method B): Synthetic Method of Indole Derivatives (1)

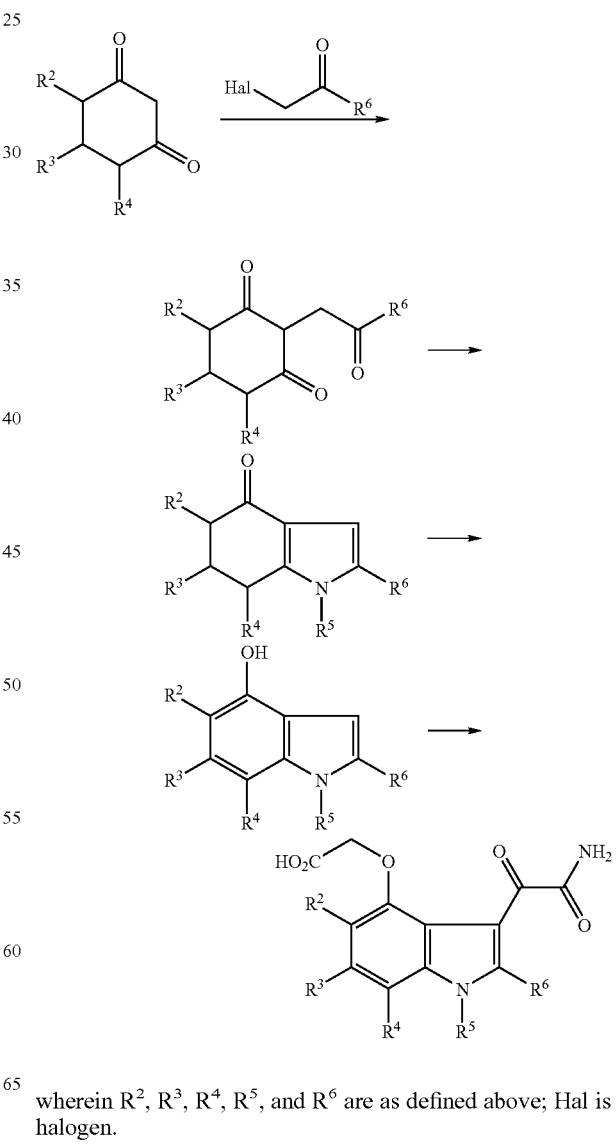

wherein $R^2$, $R^3$, $R^4$, $R^5$, and $R^6$ are as defined above; Hal is halogen.

(Method C): Synthetic Method of pyrro[1,2-a]pyrazine Derivatives
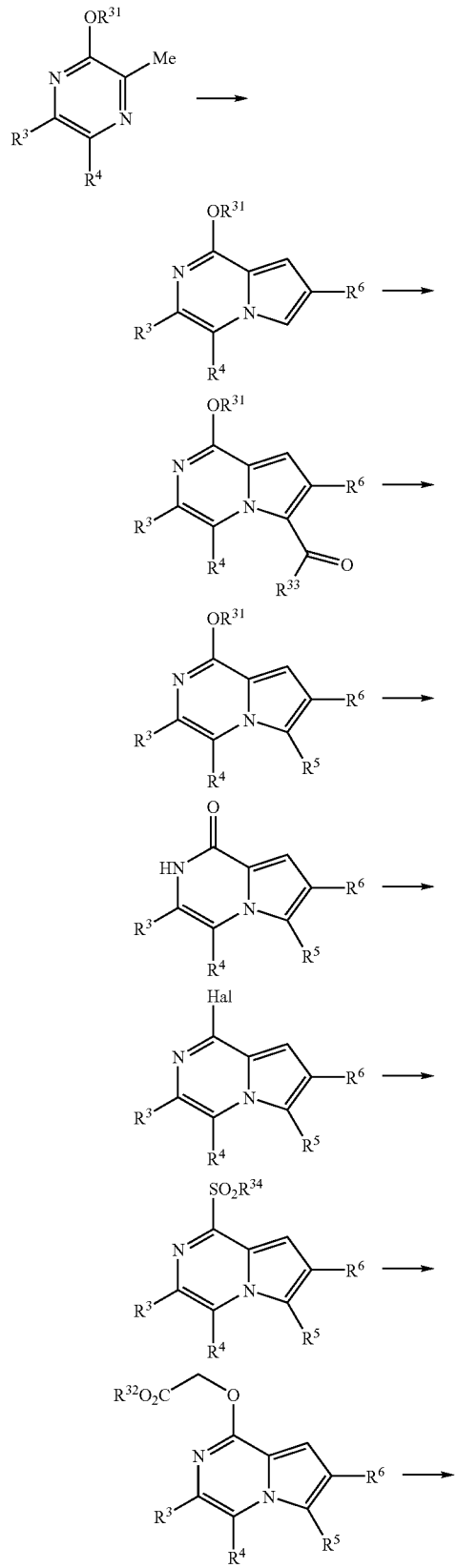
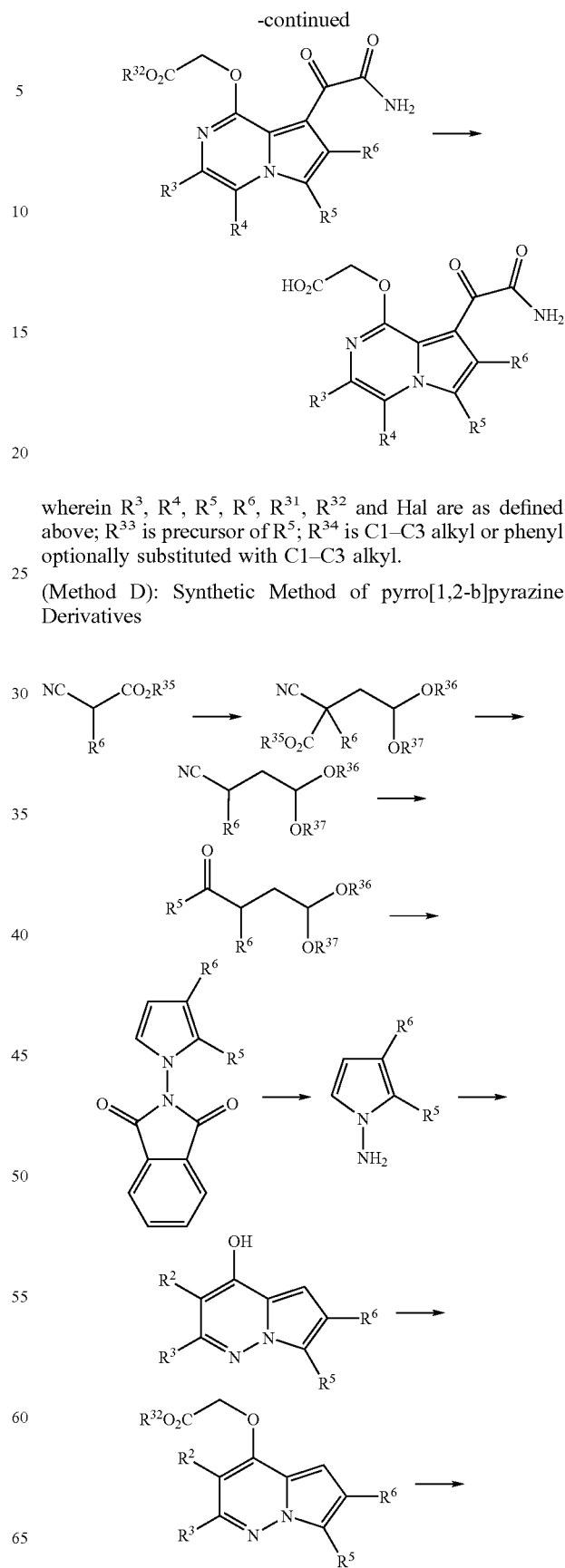
wherein $R^3$, $R^4$, $R^5$, $R^6$, $R^{31}$, $R^{32}$ and Hal are as defined above; $R^{33}$ is precursor of $R^5$; $R^{34}$ is C1–C3 alkyl or phenyl optionally substituted with C1–C3 alkyl.
(Method D): Synthetic Method of pyrro[1,2-b]pyrazine Derivatives -continued

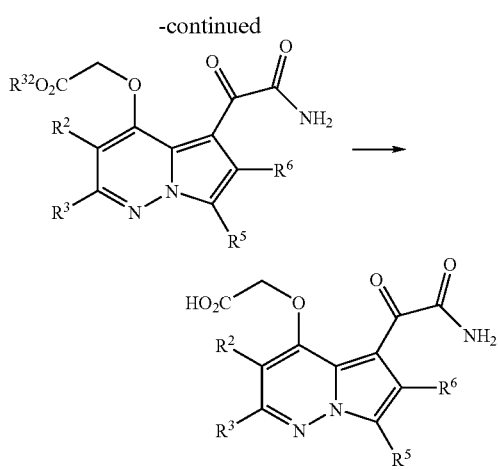

wherein $R^2$, $R^3$, $R^4$, $R^5$, $R^6$, and $R^{32}$ are as defined above; $R^{35}$ is C1–C3 alkyl; $R^{36}$ and $R^{37}$ are same or different C1–C3 alkyl, or $R^{36}$ and $R^{37}$ taken together form 1,3-dioxolane containing adjacent oxygen atom.

The preventing agent or treating agent of the present invention may be administered to a patient through a variety of routes including oral, aerosol, rectal, percutaneous, subcutaneous, intravenous, intramuscular, and nasal routes. A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In case of manufacturing a composition according to the present invention, either active ingredients are admixed with a carrier, or they are diluted with a carrier, or they are contained in a carrier in the form of capsule, sachieier, paper, or another container. In case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to prepare a formulation of compounds exhibiting type V and/or type X $sPLA_2$ inhibitory effect of the present invention prior to administration.

Any suitable carrier which has been well known by those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. An example of suitable solid carriers includes magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

The dosage varies with the conditions of the disease, administration route, age and body weight of patient. In the case of intravenous administration, the dosage can generally be between 0.01 to 10 mg/kg/hr for adult. Preferably 0.1 to 1 mg/kg/hr.

The compounds of the present invention selectively inhibit type X $sPLA_2$. The inhibitor against type X $sPLA_2$ is useful for treating or preventing inflammatory disease, cancer (especially, large bowel cancer, lung cancer, bronchogenic cancer, liver cancer, stomach cancer, gallbladder cancer, prostatic cancer, pancreatic cancer, testicular cancer, ovarian cancer, cutaneous cancer, and the like), hepatocirrhosis, Alzheimer's disease, arteriosclerosis, and the like. The term, "inflammatory diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, chronic rheumatism, stroke, cerebral infarction, heart failure, cardiac infarction, psoriasis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula (I) in an amount sufficient to inhibit $sPLA_2$ mediated release of fatty acid and to thereby inhibit or prevent the arachidonic acid cascade and its deleterious products.

EXAMPLES

The following examples are provided to further illustrate the present invention and are not to be constructed as limiting the scope thereof.

Abbreviations described below are used in the following examples.

Me: methyl
Et: ethyl
n-Pr: n-propyl
i-Pr: i-propyl
n-Bu: n-butyl
i-Bu: i-butyl
t-Bu: t-butyl
n-Pen: n-pentyl
c-Pen: cyclopentyl
c-Hex: cyclohexyl
Ph: phenyl
Bn: benzyl
4-F-Bn: 4-fluorobenzyl
Tol: tolyl
Boc: t-butoxycarbonyl
DMSO: dimethylsulfoxide

Example 1

Preparation of Compound (I-1)

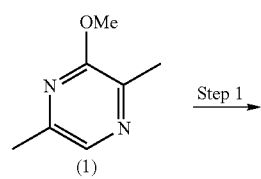
(1)

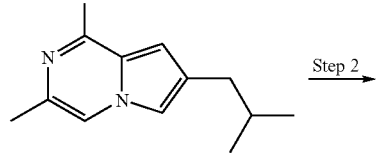
(2)

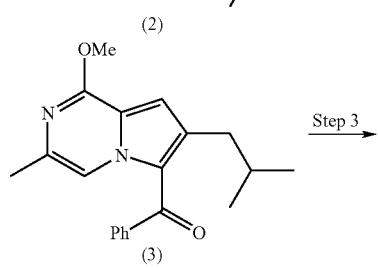
(3)

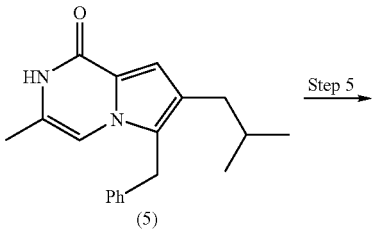
(4)

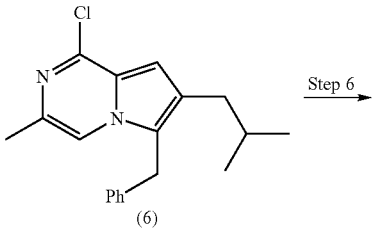
(5)

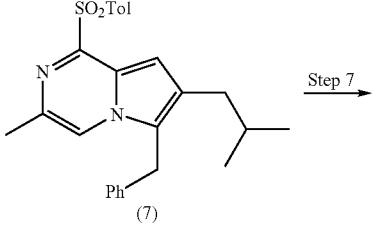
(6)

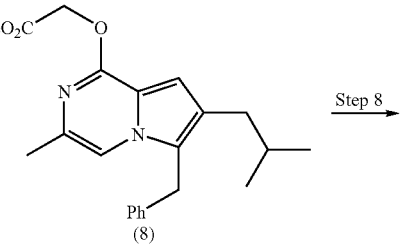
(7)

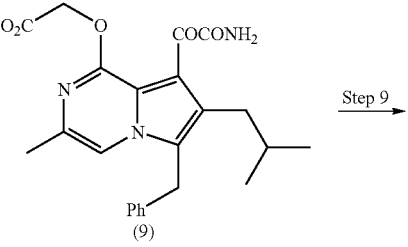
(8)

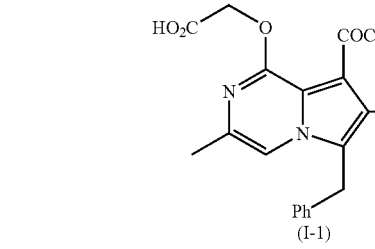
(9)

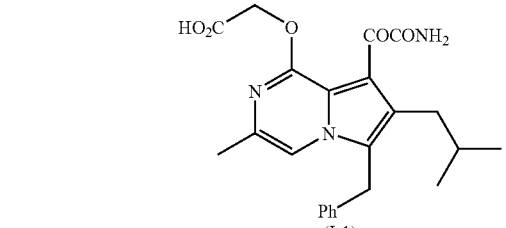
(I-1)

(Step 1)

A mixture of 3-methoxy-2,5-dimethylpyrazine (1) (3.24 g, 23.4 mmol) and 1-bromo-4-methyl-2-pentanone (4.2 g, 23.5 mmol) was stirred at 60° C. for 12 h. The resulting quarternary salts were filtered, washed with ether, and dried. The obtained quarternary salts were dissolved in acetonitrile (25 mL), and 1,8-diazabicyclo[5.4.0]-7-undecene (DBU) (5.26 mL, 35.2 mmol) was added to the reaction mixture, and the reaction mixture was heated under reflux for 1 h. A mixture of ice and water was added to the reaction mixture, and the reaction mixture was extracted with ethyl acetate. The organic layer was washed with brine, and dried over sodium sulfate. The solvent was removed, the residue was subjected to silica gel column chromatography (ethyl acetate:hexane=10:90) to give the desired compound (2) (3.63 g, 71%) as a yellow oil.

$^1$H-NMR(CDCl$_3$): 0.92(6H, d, J=6.6 Hz), 1.85(1H, m), 2.26(3H, s), 2.48(2H, d, J=7.2 Hz), 4.03(3H, s), 6.50(1H, s), 7.02(1H, s), 7.23(1H, s).

(Step 2)

To a solution of benzoyl chloride (3.2 mL, 27.6 mmol) in nitromethane (20 mL) was added aluminum chloride (3.68 g, 27.6 mmol) under ice-cooling, and the reaction mixture was stirred for 10 min. To the reaction mixture under same condition was added a solution of compound (2) (2.01 g, 9.2 mmol) in nitromethane (10 mL), and the reaction mixture was stirred for 40 min. A mixture of ice and water was added to the reaction mixture, and the reaction mixture was extracted with ethyl acetate. The organic layer was washed with aqueous ammonium hydroxide solution and brine, successively, and dried over sodium sulfate. The solvent was removed, and the residue was subjected to silica gel column chromatography (ethyl acetate:hexane=5:95) to give the desired compound (3) (886 mg, 30%) as yellow powder.

$^1$H-NMR(CDCl$_3$): 0.63(6H, d, J=6.6 Hz), 1.57(1H, m), 2.19(2H, d, J=7.2 Hz), 2.35(3H, s), 4.09(3H, s), 6.57(1H, s), 7.46(2H, m), 7.56(1H, m), 7.65(2H, m), 8.52(1H, s).

(Step 3)

To a solution of compound (3) (853 mg, 2.65 mmol) in tetrahydrofuran (10 mL) were added sodium borohydride (0.5 g, 13.2 mmol) and aluminum chloride (1.06 g, 7.95 mmol) under ice-cooling, and the reaction mixture was stirred at room temperature for 30 min. A mixture of ice and water was added to the reaction mixture, and the reaction mixture was extracted with ethyl acetate. The organic layer was washed with brine, and dried over sodium sulfate. The solvent was removed, and the residue was used at next reaction without further purification.

(Step 4)

To the above obtained residue was added concentrated hydrochloric acid (10 mL), and the reaction mixture was heated under reflux for 30 min. A mixture of ice and water was added to the reaction mixture, and the reaction mixture was extracted with ethyl acetate. The organic layer was washed with brine, and dried over sodium sulfate. The solvent was removed, and the residue was washed with a mixture of ether and hexane to give the desired compound (5) (586 mg, 90%) as gray powder.

$^1$H-NMR(d$_6$-DMSO): 0.84(6H, d, J=6.6 Hz), 1.75(1H, m), 1.96(3H, s), 2.38(2H, d, J=6.9 Hz), 4.14(2H, s), 6.69 (1H, s), 6.85(1H, s), 7.05(2H, m), 7.17(1H, m), 7.27(2H, m), 10.37(1H, brs).

(Step 5)

To compound (5) was phosphorus oxychloride (3 mL), and the reaction mixture was heated under reflux for 30 min. The reaction mixture was poured into a mixture of ice and water, and neutralized with sodium hydrogencarbonate solution. The reaction mixture was extracted with ethyl acetate, washed with brine, and dried over sodium sulfate. The solvent was removed to give a brown oil. The oil was used at next reaction without further purification.

(Step 6)

The above obtained oil was dissolved in ethanol (20 mL), and to the reaction mixture was added sodium p-toluenesulfinate (834 mg, 4.68 mmol), and the reaction mixture was heated under reflux for 18 h. The solvent was removed, and the residue was subjected to silica gel column chromatography (ethyl acetate:hexane=40:60) to give the desired compound (7) (686 mg, 68%) as yellow powder.

$^1$H-NMR(CDCl$_3$): 0.94(6H, d, J=6.6 Hz), 1.95(1H, m), 2.30(3H, s), 2.41(3H, s), 2.61(2H, d, J=7.2 Hz), 4.23(2H, s), 6.95(2H, m), 7.20–7.32(6H, m), 7.41(1H, s), 8.01(2H, d, J=8.4 Hz).

(Step 7)

To a solution of methyl glycolate (700 mg, 7.77 mmol) in tetrahydrofuran (10 mL) was added potassium t-butoxide (523 mg, 4.66 mmol) under ice-cooling, and the reaction mixture was stirred at room temperature for 30 min. To the reaction mixture was added a solution of compound (7) (672 mg, 1.55 mmol) in tetrahydrofuran (5 mL) and the reaction mixture was stirred at room temperature for 45 min. A mixture of ice and water was added to the reaction mixture, and the reaction mixture was extracted with ethyl acetate. The organic layer was washed with brine, and dried over sodium sulfate. The solvent was removed, and the residue was subjected to silica gel column chromatography (ethyl acetate:hexane=10:90) to give the desired compound (8) (545 mg, 96%) as pale yellow powder.

$^1$H-NMR(CDCl$_3$): 0.91(6H, d, J=6.6 Hz), 1.87(1H, m), 2.12(3H, s), 2.15(2H, d, J=7.5 Hz), 3.78(3H, s), 4.18(2H, s), 5.00(2H, s), 6.72(1H, s), 6.95(1H, s), 7.00(2H, m), 7.23(3H, m).

(Step 8)

To a solution of compound (8) (503 mg, 1.37 mmol) in methylene chloride (10 mL) were added N-methylmorpholine (755 μL, 6.86 mmol) and oxalyl chloride (599 μL, 6.86 mmol), and the reaction mixture was stirred at room temperature for 1 h. The reaction mixture was poured into aqueous ammonium hydroxide solution, extracted with ethyl acetate. The organic layer was washed with 1 mol/L hydrochloric acid and brine, successively, and dried over sodium sulfate. The solvent was removed, and the residue was subjected to silica gel column chromatography (chloroform:methanol=99:1) to give the desired compound (9) (414 mg, 69%) as yellow crystals.

m.p.: 163–164° C. $^1$H-NMR(d$_6$-DMSO): 0.81(6H, d, J=6.9 Hz), 1.72(1H, m), 2.15(3H, s), 2.67(2H, d, J=7.2 Hz), 3.66(3H, s), 4.32(2H, s), 4.88(2H, s), 7.07(2H, m), 7.20(1H, m), 7.29(2H, m), 7.49(1H, brs), 7.65(1H, s), 7.87(1h, brs).

(Step 9)

Compound (9) (414 mg, 0.95 mmol) was dissolved in a mixture of methanol (4 mL) and tetrahydrofuran (4 mL), and to the reaction mixture was added 1 mol/L aqueous sodium hydroxide solution (1.9 mL), and the reaction mixture was stirred at room temperature for 30 min. A mixture of ice and water was added to the reaction mixture, and the reaction mixture was acidified with 1 mol/L hydrochloric acid (4 mL), extracted with ethyl acetate. The organic layer was washed with brine, and dried over sodium sulfate. The solvent was removed, and the residue was recrystallized from ethyl acetate/hexane to give the desired compound (I-1) (366 mg, 91%) as yellow crystals.

m.p.: 206–208° C. $^1$H-NMR(d$_6$-DMSO): 0.81(6H, d, J=6.6 Hz), 1.73(1H, m), 2.16(3H, s), 2.66(2H, d, J=6.9 Hz), 4.32 (2H, s), 4.80(2H, s), 7.06–7.31(5H, m), 7.49(1H, brs), 7.63(1H, s), 7.87(1H, brs).

Compounds (I-2) to (I-8) shown in Table 1 were synthesized according to Example 1. The physical data were shown in Table 1.

TABLE 1

| Compound No. | $R^{39}$ | $R^{40}$ | m.p. (° C.) | $^1$H-NMR($d_6$-DMSO) |
|---|---|---|---|---|
| I-2 | i-Bu | c-Hex | 209–210 | 0.83(6H, d, J=6.6Hz), 1.11(5H, m), 1.60(6H, m), 1.74(1H, m), 2.26(3H, s), 2.59(2H, d, J=7.2Hz), 2.75(2H, d, J=7.5Hz), 4.79(2H, s), 7.45(1H, br.s), 7.82(2H, br.s). |
| I-3 | i-Bu | c-Pen | 193–194.5 | 0.83(6H, d, J=6.6Hz), 1.22(2H, m), 1.48(2H, m), 1.65(4H, m), 1.74(1H, m), 2.14(1H, m), 2.26(3H, s), 2.61(2H, d, J=6.9Hz), 2.87(2H, d, J=7.5Hz), 4.79(2H, s), 7.44(1H, br.s), 7.81(1H, s), 7.85(1H, s). |
| I-4 | i-Bu | Bn | 202–203 | 0.83(6H, d, J=6.6Hz), 1.71(1H, m), 2.87(3H, s), 2.48(2H, d, J=6.6Hz), 2.83(2H, t, J=7.8Hz), 3.14(2H, t, J=7.8Hz), 4.80(2H, s), 7.28(5H, m), 7.44(1H, br.s), 7.81(1H, br.s), 7.84(1H, s). |
| I-5 | n-Bu | Ph | 205–207 | 0.82(3H, t, J=7.2Hz), 1.29(2H, m), 1.38(2H, m), 2.17(3H, s), 2.73(2H, t, J=7.2Hz), 4.32(2H, s), 4.80(2H, s), 7.08–7.31(5H, m), 7.49(1H, br.s), 7.70(1H, s), 7.87(1H, br.s). |
| I-6 | n-Pen | Ph | 200–202 | 0.79(3H, t, J=7.5Hz), 1.22(4H, m), 1.40(2H, m), 2.17(3H, s), 2.72(2H, t, J=7.5Hz), 4.32(2H, s), 4.80(2H, s), 7.08–7.31(5H, m), 7.48(1H, br.s), 7.70(1H, s), 7.87(1H, br.s). |
| I-7 | Bn | Ph | 258–260 | 2.17(3H, s), 4.20(2H, s), 4.28(2H, s), 4.81(2H, s), 6.97(2H, m), 7.16(8H, m), 7.50(1H, br.s), 7.65(1H, s), 7.90(1H, br.s). |
| I-8 | CH$_2$-c-Pen | Ph | 220–221.5 | 1.14(2H, m), 1.38(2H, m), 1.55(4H, m), 1.97(1H, m), 2.16(3H, s), 2.49(2H, d, J=6.9Hz), 4.34(2H, s), 4.80(2H, s), 7.06–7.31(5H, m), 7.49(1H, br.s), 7.62(1H, s), 7.87(1H, br.s). |

Example 9

Preparation of Compound (I-9)

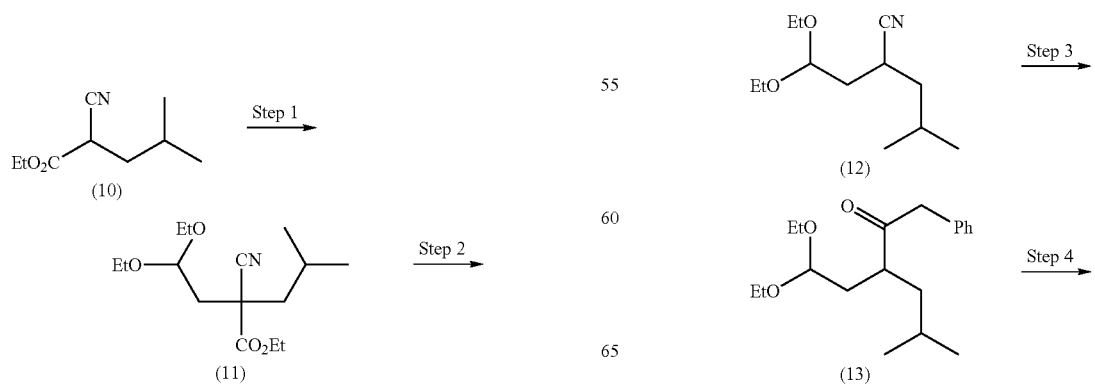

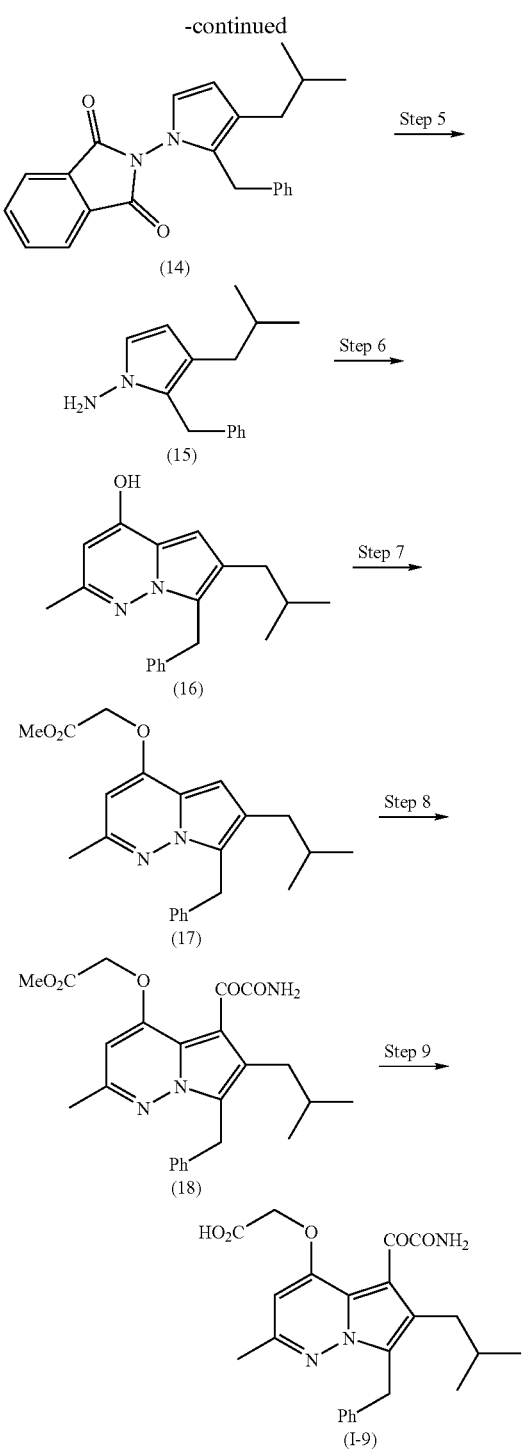

residue was distilled under reduced pressure to give the desired compound (11) (35.4 g, 78%) having boiling point between 100 to 103° C. (under 1 mm Hg) as a yellow oil.

$^1$H-NMR(CDCl$_3$): 0.91(3H, d, J=6.6 Hz), 1.06(3H, d, J=6.6 Hz), 1.17(3H, t, J=7.2 Hz), 1.21(3H, t, J=7.2 Hz), 1.33(3H, t, J=7.2 Hz), 1.65–1.91(3H, m), 1.97(1H, dd, J=14.1, 3.9 Hz), 2.38(1H, dd, J=14.1, 8.4 Hz), 3.55(2H, m), 3.66(2H, m), 4.23(2H, m), 4.78(1H, dd, J=8.4, 3.6 Hz).

(Step 2)

To a solution of compound (11) (35.3 g, 124 mmol) in dimethylsulfoxide (70 mL) was added potassium acetate (13.4 g, 137 mmol), the reaction mixture was stirred at 160° C. for 7 h. A mixture of ice and water was added to the reaction mixture, and the reaction mixture extracted with ether. The organic layer was washed with brine, and dried over sodium sulfate. The solvent was removed, and the residue was distilled under reduced pressure to give the desired compound (12) (22.1 g, 84%) having boiling point between 67 to 71° C. (under 1 mm Hg) as a colorless oil.

$^1$H-NMR(CDCl$_3$): 0.94(3H, d, J=6.3 Hz), 0.96(3H, d, J=6.3 Hz), 1.22(3H, t, J=7.2 Hz), 1.23(3H, t, J=7.2 Hz), 1.33(1H, m), 1.61(1H, m), 1.85(3H, m), 2.74(1H, m), 3.56(2H, m), 3.70(2H, m), 4.69(1H, dd, J=7.2, 3.2 Hz).

(Step 3)

To a Grignard's reagent prepared by magnesium (427 mg, 17.6 mmol), ether (10 mL), 1,2-dibromoethane (73 μL, 0.85 mmol), and benzyl bromide (2 mL, 16.8 mmol) was added a solution of compound (12) (3 g, 14.1 mmol) in ether (10 mL), and the reaction mixture was stirred at room temperature for 2.5 h and heated under reflux for 18 h. The reaction mixture was cooled at 0° C., and to the reaction mixture were added aqueous ammonium chloride (1.5 g, 28 mmol) solution (15 mL), and then 2 mol/L sulfuric acid (35 mL), and the reaction mixture was stirred for 30 min. The reaction mixture was extracted with ether, washed with brine, and dried oved sodium sulfate. The solvent was removed, and the residue was subjected to silica gel column chromatography (ethyl acetate:hexane=5:95) to give the desired compound (13) (2.2 g, 51%) as a yellow oil.

$^1$H-NMR(CDCl$_3$): 0.81(6H, d, J=6.3 Hz), 1.15(3H, t, J=7.2 Hz), 1.18(3H, t, J=7.2 Hz), 1.45(2H, m) 1.64(1H, m), 2.00(2H, m), 2.85(1H, m), 3.27–3.62(4H, m), 3.77(2H, s), 4.35(1H, t, J=5.4 Hz), 7.19–7.34(5H, m).

(Step 4)

To a solution of compound (13) (2.2 g, 7.2 mmol) in 95% ethanol (50 mL) were added N-aminophthalimide (2.28 g, 14.1 mmol) and 1 mol/L hydrochloric acid (1.4 mL), the reaction mixture was heated under reflux for 30 min. The reaction mixture was cooled, and the resulting precipitates were filtered and washed with ethanol to give the desired compound (14) (1.96 g, 76%) as pale yellow crystals.

$^1$H-NMR(CDCl$_3$): 0.96(6H, d, J=6.9 Hz), 1.85(1H, m), 2.37(2H, d, J=6.9 Hz), 3.81(2H, s), 6.18(1H, d, J=3.3 Hz), 6.59(1H, d, J=3.3 Hz), 6.97(5H, m), 7.77(4H, m).

(Step 5)

To a solution of compound (14) (1 g, 2.79 mmol) in ethanol (10 ml) was added hydrazine monohydrate (350 mg, 6.99 mmol), and the reaction mixture was heated under reflux for 1 h. The indissoluble substance was filtered off, and the solvent of filtrate was removed. The residue was subjected to silica gel column chromatography (ethyl acetate:hexane=10:90) to give the desired compound (15) (578 mg, 91%) as a colorless oil.

¹H-NMR(CDCl₃): 0.90(6H, d, J=6.9 Hz), 1.75(1H, m), 2.29(2H, d, J=6.9 Hz), 3.98(2H, s), 4.32(2H, s), 5.88(1H, d, J=2.7 Hz), 6.64(1H, d, J=2.7 Hz), 7.07–7.29(5H, m).

(Step 6)

To a solution of compound (15) (568 mg, 2.49 mmol) in chloroform (15 ml) were methyl acetoacetate (289 mg, 2.49 mmol) and p-toluenesulfonic acid monohydrate (24 mg, 0.13 mmol), and the reaction mixture was heated under reflux for 4 h. The resulting water was removed through Dean-Stark filled up molecular sieves 4 A. The reaction mixture was diluted with chloroform, washed with saturated aqueous sodium hydrogencarbonate solution and brine, successively, and dried over sodium sulfate. The solvent was removed, and the residue was subjected to silica gel column chromatography (ethyl acetate:hexane=15:85) to give the desired compound (16) (692 mg, 94%) as a brown oil.

¹H-NMR(CDCl₃): 0.89(6H, d, J=6.6 Hz), 1.84(1H, m), 2.35(3H, s), 2.49(2H, d, J=6.9 Hz), 4.36(2H, s), 5.80(1H, s), 6.38(1H, s), 7.13–7.24(5H, m).

(Step 7)

To a solution of compound (16) (685 mg, 2.33 mg) in N,N-dimethylformaide (10 mL) were added methyl bromoacetoacetate (463 mg, 3.02 mmol) and potassium carbonate (418 mg, 3.02 mmol), and the reaction mixture was stirred at room temperature for 1.5 h. A mixture of ice and water was added to the reaction mixture, and the reaction mixture extracted with ethyl acetate. The organic layer was washed with brine and dried over sodium sulfate. The solvent was removed, and the residue was subjected to silica gel column chromatography (ethyl acetate:hexane=10:90) to give the desired compound (17) (718 mg, 84%) as yellow powder.

¹H-NMR(CDCl₃): 0.89(6H, d, J=6.3 Hz), 1.85(1H, m), 2.37(3H, s), 2.48(2H, d, J=6.9 Hz), 3.83(3H, s), 4.34(2H, s), 4.76(2H, s), 5.60(1H, s), 6.49(1H, s), 7.13–7.24(5H, m).

(Step 8)

To a solution of compound (17) (685 mg, 1.74 mmol) in methylene chloride (10 mL) were added N-methylmorpholine (954 μL, 8.68 mmol) and oxalyl chloride (757 μL, 8.68 mmol), the reaction mixture was stirred at room temperature for 30 min. The reaction mixture was poured into aqueous ammonium hydroxide solution and extracted with ethyl acetate. The organic layer was washed with 1 mol/L hydrochloric acid and brine, successively, and dried over sodium sulfate. The solvent was removed, and the residue was subjected to silica gel column chromatography (chloroform:methanol=98:2) to give the desired compound (18) (604 mg, 80%) as pale yellow crystals.

m.p.: 205.5–207.5° C. ¹H-NMR(d₆-DMSO): 0.80(6H, d, J=6.6 Hz), 1.74(1H, m), 2.39(3H, s), 2.65(2H, d, J=7.2 Hz), 3.72(3H, s), 4.31(2H, s), 4.94(2H, s), 6.48(1H, s), 7.14–7.27 (5H, m), 7.35(1H, brs), 7.73(1H, brs).

(Step 9)

Compound (18) (300 mg, 0.69 mmol) was dissolved in tetrahydrofuran (8 mL) and methanol (8 mL) and to the reaction mixture was added 1 mol/L aqueous sodium hydroxide solution (1.37 mL), and the reaction mixture was stirred at room temperature for 1 h. The reaction mixture was acidified with 1 mol/L hydrochloric acid and extracted with ethyl acetate. The organic layer was washed with brine and dried over sodium sulfate. The solvent was removed, and the residue was recrystallized from methanol to give the desired compound (I-9) (168 mg, 58%) as yellow crystals.

m.p.: 245–247° C. ¹H-NMR(d₆-DMSO): 0.80(6H, d, J=6.6 Hz), 1.75(1H, m), 2.38(3H, s), 2.64(2H, d, J=7.2 Hz), 4.31(2H, s), 4.82(2H, s), 6.42(1H, s), 7.14–7.27(5H, m), 7.37(1H, brs), 7.74(1H, brs).

Example 10

Preparation of Compound (I-10)

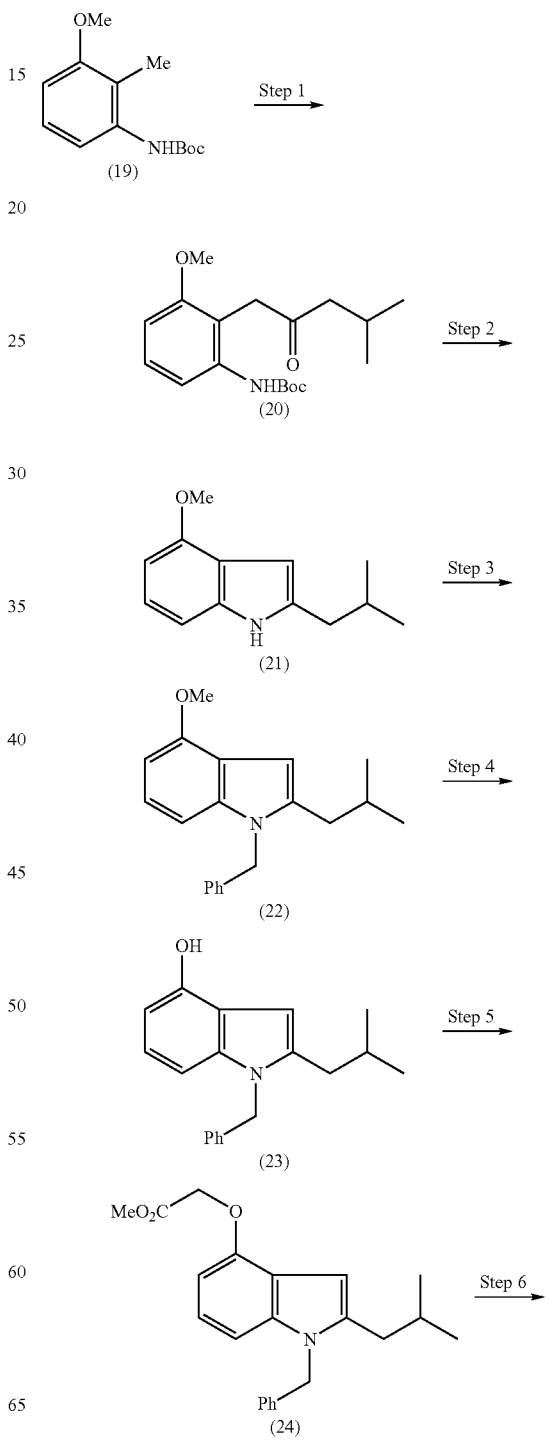

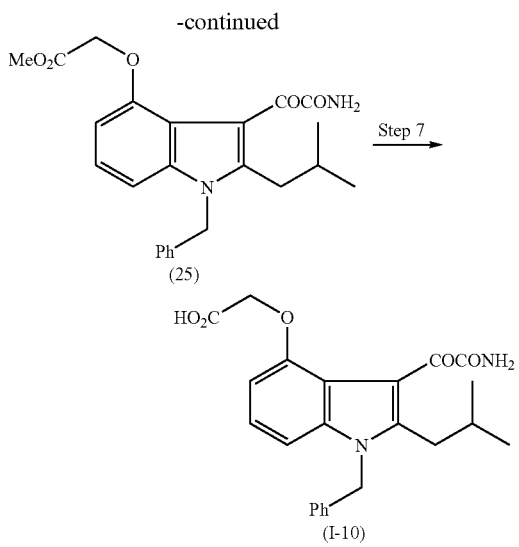

-continued (25)

(I-10)

(Step 1)

A solution of compound (19) (4 g, 16.7 mmol) in tetrahydrofuran (70 ml) was cooled at −40° C. and to the reaction mixture was added 1M sec-butyllithium-cyclohexane/hexane solution (33.8 mL) was added dropwise slowly. After the reaction mixture was stirred for 15 min, to the reaction mixture was added dropwise a solution of n-methoxy-3,N-dimethyl-butyramide (2.45 g, 16.9 mmol) in tetrahydrofuran (25 mL) at −40° C. The reaction mixture was stirred at −40° C. for 1 h and at room temperature for 1 h. The reaction mixture was poured into a mixture of 1 mol/L hydrochloric acid and ether, and extracted with ether. The organic layer was washed with brine and dried over sodium sulfate. The solvent was removed to give a crude compound (20). The crude compound was used at next reaction without further purification.

(Step 2)

The crude compound (20) was dissolved in methylene chloride (40 mL) and to the reaction mixture was added trifluoroacetic acid (16 mL), and the reaction mixture was stirred at room temperature for 1.5 h. The solvent was removed and the residue was diluted with chloroform. The organic layer was washed with saturated aqueous sodium hydrogencarbonate solution and brine, successively, and dried over sodium sulfate. The solvent was removed, and the residue was subjected to silica gel column chromatography (ethyl acetate:hexane=10:90) to give the desired compound (21) (1.06 g, 31%) as a brown oil.

$^1$H-NMR(CDCl$_3$): 0.97(6H, d, J=6.9 Hz), 1.97(1H, m), 2.60(2H, d, J=7.2 Hz), 3.95(3H, s), 6.33(1H, s), 6.51(1H, d, J=7.8 Hz), 6.94(1H, d, J=7.8 Hz), 7.04(1H, t, J=7.8 Hz), 7.85(1H, brs).

(Step 3)

To a solution of compound (21) (572 mg, 2.81 mmol) in N,N-dimethylformaide (6 ml) was added 60% sodium hydride (124 mg, 3.1 mmol), the reaction mixture was stirred at room temperature for 1 h. To the reaction mixture was added benzyl chloride (389 μL, 3.38 mmol) and the reaction mixture was stirred for 1 h. A mixture of ice and water was added to the reaction mixture and the reaction mixture was extracted with ethyl acetate. The solvent was removed, and the residue was subjected to silica gel column chromatography (ethyl acetate:hexane=10:90) to give the desired compound (22) (803 mg, 97%) as a yellow oil.

$^1$H-NMR(CDCl$_3$): 0.95(6H, d, J=6.6 Hz), 1.92(1H, m), 2.53(2H, d, J=7.2 Hz), 3.97(3H, s), 5.30(2H, s), 6.44(1H, s), 6.52(1H, d, J=8.1 Hz), 6.80(1H, d, J=8.1 Hz), 6.94(2H, m), 7.01(1H, t, J=8.1 Hz), 7.22(3H, m).

(Step 4)

To a solution of compound (22) (803 mg, 2.74 mmol) in methylene chloride (10 mL) was added dropwise 1M boron tribromide/methylene chloride solution (5.47 mL), and the reaction mixture was stirred at room temperature for 1 h. The reaction mixture was poured into a mixture of ice and water, and extracted with chloroform. The organic layer was washed with brine, dried over sodium sulfate, and the solvent was removed. The residue was subjected to silica gel column chromatography (ethyl acetate:hexane=20:80) to give the desired compound (23) (638 mg, 83%) as brown powder.

$^1$H-NMR(CDCl$_3$): 0.96(6H, d, J=6.6 Hz), 1.92(1H, m), 2.54(2H, d, J=7.2 Hz), 4.96(1H, s), 5.29(2H, s), 6.37(1H, s), 6.50(1H, d, J=8.1 Hz), 6.78(1H, d, J=8.1 Hz), 6.94(3H, m), 7.23(3H, m).

(Step 5)

Compound (23) (638 mg, 2.28 mmol) was dissolved in N,N-dimethylformamide (6 mL), to the reaction mixture was added potassium carbonate (568 mg, 4.11 mmol), and the reaction mixture was stirred for 30 min. To the reaction mixture were added methyl bromoacetate (259 μL, 2.74 mmol) and potassium iodide (38 mg, 0.23 mmol), and the reaction mixture was stirred at room temperature for 1.5 h. To the reaction mixture was added a mixture of ice and water, the reaction mixture was extracted with ethyl acetate. The organic layer was washed brine, and dried over sodium sulfate. The solvent was removed, and the residue was subjected to silica gel column chromatography (ethyl acetate:hexane=10:90) to give the desired compound (24) (596 mg, 74%) as white powder.

$^1$H-NMR(CDCl3): 0.95(6H, d, J=6.6 Hz), 1.93(1H, m), 2.54(2H, d, J=6.9 Hz), 3.82(3H, s), 4.80(2H, s), 5.30(2H, s), 6.41(1H, d, J=7.8 Hz), 6.51(1H, s), 6.84(1H, d, J=7.8 Hz), 6.93(2H, m), 6.97(1H, t, J=7.8 Hz), 7.23(3H, m).

(Step 6)

Compound (24) (596 mg, 1.70 mmol) was dissolved in methylene chloride (10 mL), and to the reaction mixture was added oxalyl chloride (163 μL, 1.87 mmol), and the reaction mixture was stirred at room temperature for 1 h and 20 min. To the reaction mixture was added aqueous ammonium hydroxide solution, and the reaction mixture was extracted with ethyl acetate. The organic layer was washed brine, and dried over sodium sulfate. The solvent was removed, and the residue was recrystallized from ethyl acetate/hexane to give the desired compound (25) (644 mg, 90%) as colorless crystals.

m.p.: 167–168.5° C. $^1$H-NMR(d$_6$-DMSO): 0.87(6H, d, J=6.3 Hz), 1.85(1H, m), 2.86(2H, d, J=7.5 Hz), 3.71(3H, s), 4.76(2H, s), 5.51(2H, s), 6.56(1H, dd, J=1.8, 6.3 Hz), 7.02(4H, m), 7.29(3H, m), 7.35(1H, brs), 7.70(1H, brs).

(Step 7)

Compound (25) (639 mg, 1.51 mmol) was dissolved in a mixture of tetrahydrofuran (10 mL) and methanol (10 mL), and to the reaction mixture was added 1 mol/L aqueous sodium hydroxide solution (3.0 mL), and the reaction mixture was stirred at room temperature for 1.5 h. The reaction mixture was acidified with 1 mol/L hydrochloric acid and extracted with ethyl acetate. The organic layer was washed brine, and dried over sodium sulfate. The solvent was removed, and the residue was recrystallized from ethyl acetate/hexane to give the desired compound (I-10) (561 mg, 91%) as colorless crystals.

m.p.: 208.5–210° C. $^1$H-NMR($d_6$-DMSO): 0.87(6H, d, J=6.6 Hz), 1.85(1H, m), 2.86(2H, d, J=7.2 Hz), 4.65(2H, s), 5.51(2H, s), 5.52(1H, d.d, J=1.2, 7.2 Hz), 7.00(4H, m), 7.29(3H, m), 7.40(1H, brs), 7.74(1H, brs).

Compounds (I-11) and (I-12) shown in Table 2 were synthesized according to Example 10. The physical data were shown in Table 2.

TABLE 2

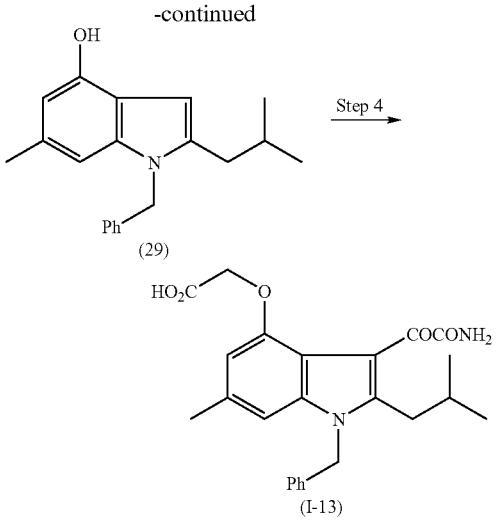

| Compound No. | R[41] | m.p. (° C.) | $^1$H-NMR($d_6$-DMSO) |
|---|---|---|---|
| I-11 | 4-F-Ph | 172–173.5 | 0.87(6H, d, J=6.6Hz), 1.84(1H, m), 2.86(2H, d, J=7.5Hz), 4.65(2H, s), 5.50(2H, s), 6.52(1H, d.d, J=1.2, 7.2Hz), 6.99–7.18(5H, m), 7.41(1H, br.s), 7.75(1H, br.s). |
| I-12 | c-Hex | 195.5–197 | 0.90(6H, d, J=6.6Hz), 1.11(4H, m), 1.49–1.78(6H, m), 1.93(1H, m), 2.86(2H, d, J=7.2Hz), 4.03(2H, d, J=7.5Hz), 4.63(2H, s), 6.51(1H, d, J=7.8Hz), 7.08(1H, t, J=7.8Hz), 7.15(1H, d, J=7.8Hz), 7.37(1H, br.s), 7.71(1H, br.s). |

Example 13

Preparation of Compound (I-13)

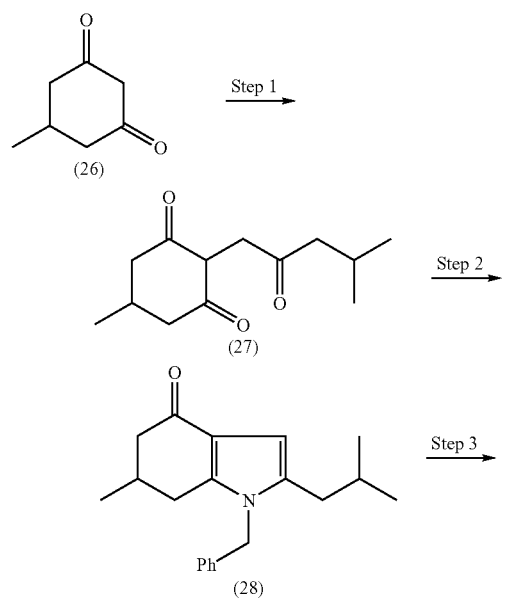

(Step 1)

5-Methyl-1,3-cyclohexanedione (26) (6.16 g, 48.8 mmol) was dissolved in acetonitrile (10 mL), and to the reaction mixture were added 1-bromo-4-methyl-2-pentanone (8.75 g, 48.9 mmol) and 1 mol/L aqueous sodium hydroxide solution (63.5 mL), and the reaction mixture was stirred at room temperature for 72 h. The reaction mixture was diluted with water, extracted with ethyl acetate, and dried over sodium sulfate. The solvent was removed, and the residue was subjected to silica gel column chromatography (ethyl acetate:hexane=50:50) to give the desired compound (27) (1.32 g, 12%) as white powder.

$^1$H-NMR(CDCl$_3$): 0.89(6H, d, J=6.6 Hz), 1.99–2.28(4H, m), 2.46(2H, d, J=7.2 Hz), 2.49(2H, m), 3.29(1H, d, J=8.1 Hz), 3.72(1H, d, J=8.1 Hz), 9.93(1H, s).

(Step 2)

To a solution of compound (27) (1.28 g, 5.71 mmol) in toluene (30 mL) was added benzylamine (612 mg, 5.71 mmol), and the reaction mixture was heated under reflux for 3 h. The resulting water was removed through Dean-Stark filled up molecular sieves 4 A. The reaction mixture was diluted with ethyl acetate, washed with 1 mol/L hydrochloric acid, and dried over sodium sulfate. The solvent was removed, and the residue was subjected to silica gel column chromatography (ethyl acetate:hexane=25:75) to give the desired compound (28) (1.43 g, 85%) as pale yellow powder.

$^1$H-NMR(CDCl$_3$): 0.90(6H, d, J=6.3 Hz), 1.08(3H, d, J=6.0 Hz), 1.78(1H, m), 2.17–2.43(5H, m), 2.50(1H, m), 2.69(1H, m), 5.03(2H, s), 6.36(1H, s), 6.89(2H, m), 7.32 (3H, m).

(Step 3)

Compound (28) (0.95 g, 3.22 mmol) was dissolved in 2-(2-ethoxyethoxy)ethanol (12 mL), and to the reaction mixture was added 10% palladium on activated carbon (190 mg), and the reaction mixture was heated at 200° C. for 9 h. The reaction mixture was diluted with ethyl acetate, washed with water and brine, successively, and dried over sodium sulfate. The solvent was removed, and the residue was subjected to silica gel column chromatography (ethyl acetate:hexane=10:90) to give the desired compound (29) (634 mg, 67%) as pale yellow powder.

¹H-NMR(CDCl₃): 0.94(6H, d, J=6.6 Hz), 1.89(1H, m), 2.34(3H, s), 2.51(2H, d, J=7.2 Hz), 4.84(1H, s), 5.25(2H, s), 6.30(1H, s), 6.35(1H, s), 6.59(1H, s), 6.94(2H, m), 7.24(3H, m).

(Step 4)

Compound (I-13) was synthesized from compound (29) as a starting material by the similar method as described in Step 5 to Step 7 of Example 10.

m.p.: 220–221.5° C. ¹H-NMR(d₆-DMSO): 0.86(6H, d, J=6.6 Hz), 1.83(1H, m), 2.29(3H, s), 2.83(2H, d, J=7.2 Hz), 4.64(2H, s), 5.47(2H, s), 6.36(1H, s), 6.83(1H, s), 6.98–7.34 (5H, m), 7.40(1H, brs), 7.74(1H, brs),12.92(1H, brs).

Example 14

Preparation of Compound (I-14)

Compound (I-14) was synthesized according to Example 13.

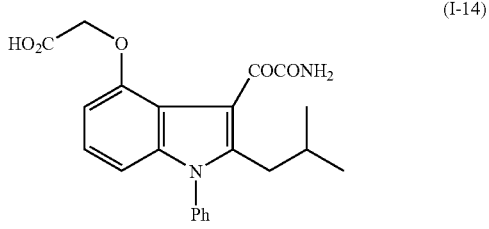

(I-14)

m.p.: 200.5–202° C. ¹H-NMR(d₆-DMSO): 0.67(6H, d, J=6.9Hz), 1.56(1H, m), 2.77(2H, d, J=6.9 Hz), 4.69(2H, s), 6.57(1H, d, J=7.8 Hz), 6.59(1H, d, J=7.8 Hz), 7.05(1H, t, J=7.8 Hz), 7.47–7.69(6H, m), 7.82(1H, brs).

Example 15

Preparation of Compound (I-15)

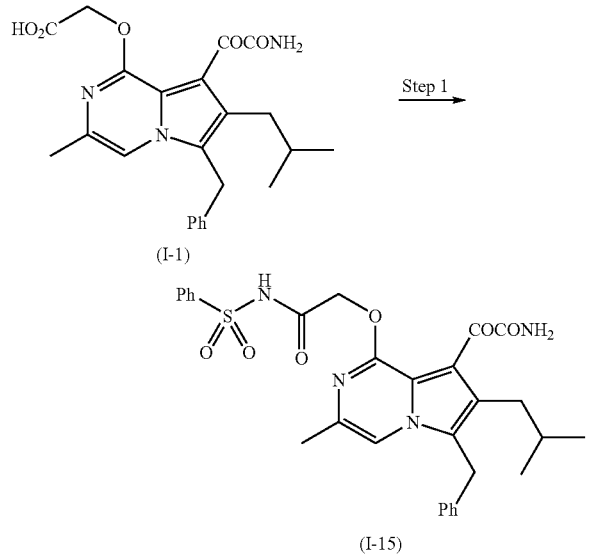

(Step 1)

Compound (I-1) (150 mg, 0.35 mmol) was dissolved in methylene chloride (10 mL), and to the reaction mixture were added benzenesulfonamide (61 mg, 0.39 mmol), 1-ethyl-3-(3-dimethylaminopropyl)carbodiimide hydrochloric acid salt (75 mg, 0.39 mmol), and 4-dimethylaminopyridine (48 mg, 0.39 mmol), and the reaction mixture was stirred at room temperature for 1 h. To the reaction mixture was 1 mol/L hydrochloric acid, the reaction mixture was extracted with chloroform. The organic layer was washed with brine and dried over sodium sulfate. The solvent was removed, and the residue was subjected to silica gel column chromatography (chloroform:methanol=95:5) to give the desired compound (I-15) (114 mg, 57%) as pale yellow crystals.

m.p.: 193–195° C. ¹H-NMR(d₆-DMSO): 0.81(6H, d, J=6.6 Hz), 1.73(1H, m), 1.90(3H, s), 2.66(2H, d, J=7.2 Hz), 4.31(2H, s), 4.76(2H, s), 7.04–7.31(5H, m), 7.54–7.71(5H, m), 7.85(2H, m), 7.96(1H, brs), 12.20(1H, brs).

Compounds (I-16) to (I-32) shown in Tables 3, 4, and 5 were synthesized according to Example 15. The physical data were shown in Tables 3, 4, and 5.

TABLE 3

| Compound No. | R | m.p. (° C.) | ¹H-NMR(d₆-DMSO) |
|---|---|---|---|
| I-16 | Me | 211–212 | 0.82(6H, d, J=6.3Hz), 1.74(1H, m), 2.17(3H, s), 2.68(2H, d, J=6.9Hz), 3.24(3H, s), 4.33(2H, s), 4.84(2H, s), 7.06–7.31(5H, m), 7.62(1H, br.s), 7.67(1H, s), 8.00(1H, br.s), 11.81(1H, br.s). |
| I-17 | Et | 214–215 | 0.82(6H, d, J=6.6Hz), 1.21(3H, t, J=7.2Hz), 1.74(1H, m), 2.16(3H, s), 2.68(2H, d, J=6.9Hz), 3.35(2H, q, J=7.2Hz), 4.33(2H, s), 4.85(2H, s), 7.06–7.31(5H, m), 7.60(1H, br.s), 7.67(1H, s), 7.99(1H, br.s), 11.75(1H, br.s). |
| I-18 | n-Pr | 205–207 | 0.82(6H, d, J=6.6Hz), 0.95(3H, t, J=7.5Hz), 1.67(2H, m), 1.74(1H, m), 2.16(3H, s), 2.68(2H, d, J=7.2Hz), 3.33(2H, t, J=7.5Hz), 4.33(2H, s), 4.85(2H, s), 7.06–7.31(5H, m), 7.60(1H, br.s), 7.68(1H, s), 7.99(1H, br.s), 11.76(1H, br.s). |
| I-19 | i-Pr | 196–198 | 0.82(6H, d, J=6.6Hz), 1.27(6H, d, J=6.9Hz), 1.74(1H, m), 2.16(3H, s), 2.68(2H, d, J=7.2Hz), 3.58(1H, m), 4.33(2H, s), 4.85(2H, s), 7.06–7.31(5H, m), 7.58(1H, br.s), 7.67(1H, s), 7.97(1H, br.s), 11.69(1H, br.s). |
| I-20 | CF₃ | — | 0.82(6H, d, J=6.6Hz), 1.75(1H, m), 2.14(3H, s), 2.64(2H, d, J=7.2Hz), 4.31(2H, s), 4.69(2H, s), 7.06–7.31(5H, m), 7.45(1H, br.s), 7.55(1H, s), 7.80(1H, br.s). |

TABLE 4

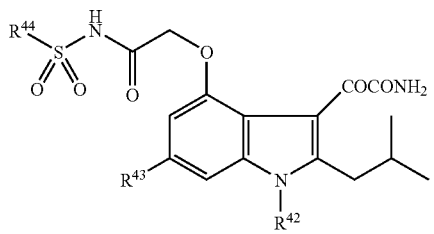

| Compound No. | R42 | R43 | R44 | m.p. (° C.) | ¹H-NMR(d₆-DMSO) |
|---|---|---|---|---|---|
| I-21 | Bn | H | Ph | 218–220 | 0.88(6H, d, J=6.6Hz), 1.87(1H, m), 2.90(2H, d, J=7.2Hz), 4.65(2H, s), 5.53(2H, s), 6.23(1H, d, J=7.8Hz), 6.91(1H, t, J=7.8Hz), 7.02(3H, m), 7.29(3H, m), 7.53(2H, m), 7.61(1H, br.s), 7.68(1H, m), 7.82(2H, m), 7.99(1H, br.s), 12.04(1H, br.s). |
| I-22 | 4-F-Bn | H | Ph | 172–173 | 0.88(6H, d, J=6.6Hz), 1.85(1H, m), 2.89(2H, d, J=7.5Hz), 4.63(2H, s), 5.51(2H, s), 6.24(1H, d, J=7.8Hz), 6.93(1H, t, J=7.8Hz), 7.02(1H, d, J=7.8Hz), 7.06(2H, m), 7.16(2H, m), 7.54(2H, m), 7.59(1H, br.s), 7.67(1H, m), 7.81(2H, m), 7.97(1H, br,s), 12.06(1H, br.s). |
| I-23 | Bn | H | Me | 207–209 | 0.88(6H, d, J=6.6Hz), 1.86(1H, m), 2.89(2H, d, J=7.2Hz), 3.18(3H, s), 4.66(2H, s), 5.23(2H, s), 6.52(1H, d.d, J=1.2, 7.2Hz), 7.04(4H, m), 7.29(3H, m), 7.58(1H, br.s), 7.96(1H, br.s), 11.68(1H, br.s). |
| I-24 | Bn | Me | Ph | 145–147 | 0.87(6H, d, J=6.3Hz), 1.86(1H, m), 2.11(3H, s), 2.86(2H, d, J=6.9Hz), 4.63(2H, s), 5.49(2H, s), 6.00(1H, s), 6.83(1H, s), 7.00(2H, m), 7.29(3H, m), 7.48(2H, m), 7.66(2H, m), 7.75(2H, m), 8.02(1H, br.s), 11.98(1H, br.s). |
| I-25 | Bn | Me | Me | 211–214 | 0.86(6H, d, J=6.6Hz), 1.84(1H, m), 2.30(3H, s), 2.85(2H, d, J=6.9Hz), 3.22(3H, s), 4.68(2H, s), 5.48(2H, s), 6.38(1H, s), 6.87(1H, s), 7.00(2H, m), 7.29(3H, m), 7.59(1H, br.s), 7.97(1H, br.s), 11.61(1H, br.s). |
| I-26 | Bn | H | Et | 200–201 | 0.88(6H, d, J=6.6Hz), 1.11(3H, t, J=7.5Hz), 1.87(1H, m), 2.90(2H, d, J=7.5Hz), 3.35(2H, q, J=7.5Hz), 4.76(2H, s), 5.53(2H, s), 6.51(1H, d.d. J=2.4, 6.0Hz), 6.99–7.10(4H, m), 7.22–7.34(3H, m), 7.62(1H, br.s), 8.02(1H, br.s), 11.53(1H, br.s). |

TABLE 5

[Structure: indole with R44-SO2-NH-CO-CH2-O- at position 4, COCONH2 at position 3, isobutyl at position 2, R42 on N1, R43 at position 6]

| Compound No. | R42 | R43 | R44 | m.p. (° C.) | 1H-NMR(d6-DMSO) |
|---|---|---|---|---|---|
| I-27 | Bn | H | n-Pr | 181–183 | 0.87(9H, m), 1.53(2H, m), 1.87(1H, m), 2.90(2H, d, J=7.2Hz), 3.31(2H, t, J=8.1Hz), 4.75(2H, s), 5.54(2H, s), 6.51(1H, d.d. J=2.7, 5.7Hz), 7.00–7.11(4H, m), 7.22–7.34(3H, m), 7.64(1H, br.s), 8.04(1H, br.s), 11.54(1H, br.s). |
| I-28 | Bn | H | i-Pr | 218.5–220 | 0.88(6H, d, J=6.3Hz), 1.17(6H, d, J=6.9Hz), 1.87(1H, m), 2.90(2H, d, J=7.5Hz), 3.54(1H, m), 4.77(2H, s), 5.54(2H, s), 6.50(1H, d, d, J=2.4, 6.3Hz), 6.98–7.10(4H, m), 7.22–7.33(3H, m), 7.62(1H, br.s), 8.03(1H, br.s), 11.44(1H, br.s). |
| I-29 | Bn | H | n-Bu | 219.5–221 | 0.78(3H, t, J=7.2Hz), 0.88(6H, d, J=6.6Hz), 1.28(2H, m), 1.47(2H, m), 1.87(1H, m), 2.90(2H, d, J=7.5Hz), 3.33(2H, t, J=7.8Hz), 4.76(2H, s), 5.53(2H, s), 6.50(1H, t, J=4.5Hz), 7.00–7.07(4H, m), 7.22–7.34(3H, m), 7.66(1H, br.s), 8.05(1H, br.s), 11.53(1H, br.s). |
| I-30 | Bn | H | CF3 | 208–210 | 0.87(6H, d, J=6.6Hz), 1.85(1H, m), 2.84(2H, d, J=7.5Hz), 4.41(2H, s), 5.49(2H, s), 6.37(1H, d, J=7.5Hz), 6.91–7.02(4H, m), 7.21–7.33(3H, m), 7.35(1H, br.s), 7.68(1H.br.s). |
| I-31 | Bn | H | Me | 159–161 | 0.68(6H, d, J=6.9Hz), 1.59(1H, m), 2.80(2H, d, J=7.2Hz), 3.27(3H, s), 4.76(2H, s), 6.59(1H, d, J=7.8Hz), 6.60(1H, d, J=7.8Hz), 7.07(1H, t, J=7.8Hz), 7.50–7.69(6H, m), 8.08(1H, br.s), 11.66(1H, br.s). |
| I-32 | [Structure: pyrrolopyridazine with Ph-SO2-NH-CO-CH2-O-, COCONH2, methyl, isobutyl, and Ph-CH2- substituents] | | | 188–190 | 0.79(6H, d, J=6.9Hz), 1.75(1H, m), 2.25(3H, s), 2.61(2H, d, J=7.2Hz), 4.29(2H, s), 4.52(2H, s), 5.95(1H, s), 7.14(3H, m), 7.23(2H, m), 7.41(4H, m), 7.74(1H, br.s), 7.76(2H, m). |

Example 33

Preparation of Compound (I-33)

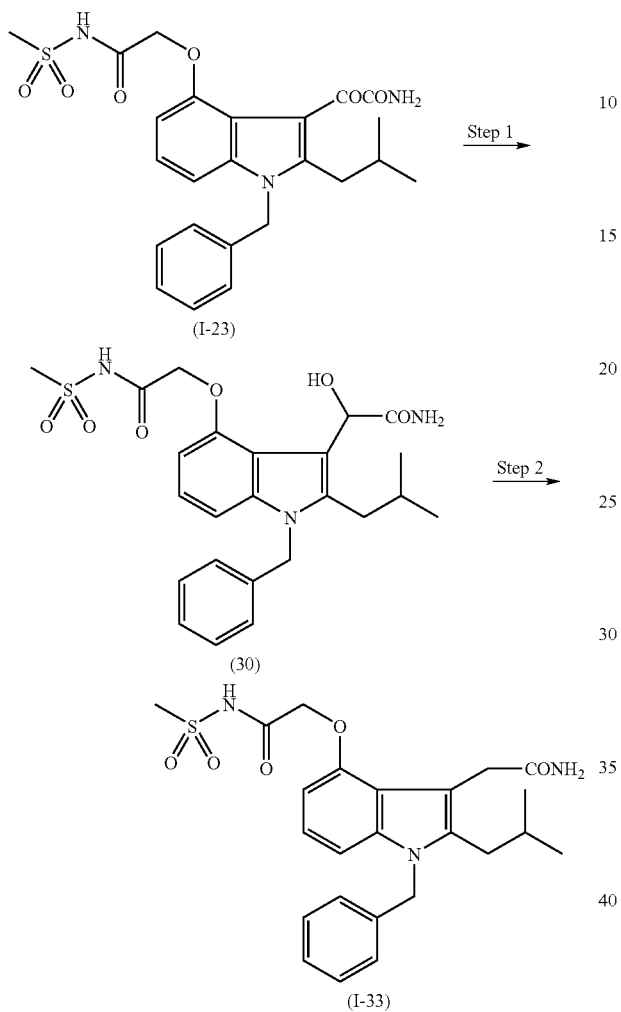

(Step 1)

To a suspension of compound (I-23) (403 mg, 0.83 mmol) in ethanol (10 ml) was added sodium borohydride (41 mg, 1.08 mmol), and the reaction mixture was stirred at 50° C. for 15 min. The reaction mixture was poured into 2 mol/L hydrochloric acid and extracted with ethyl acetate. The organic layer was washed with brine and dried over sodium sulfate. The solvent was removed to give the desired compound (30) (398 mg, 98%) as white powder. The compound was used at next reaction without further purification.

(Step 2)

To compound (30) (350 mg, 0.72 mmol) were added trifluoroacetic acid (2 mL) and triethylsilane (149 µL, 0.93 mmol), the reaction mixture was stirred at room temperature for 15 min. The reaction mixture was diluted with ethyl acetate, washed with water and brine, successively, and dried over sodium sulfate. The solvent was removed, and the residue was subjected to silica gel column chromatography (chloroform:methanol=97:3) to give the desired compound (I-33) (111 mg, 33%) as colorless crystals.

m.p.: 189–190° C. $^1$H-NMR(d$_6$-DMSO): 0.87(6H, d, J=6.6Hz), 1.74(1H, m), 2.62(2H, d, J=7.2 Hz), 3.28(3H, s), 3.69(2H, s), 4.79(2H, s), 5.38(2H, s), 6.37(1H, d, J=6.9 Hz), 6.91(5H, m), 7.06(1H, brs), 7.24(3H, m), 12.11(1H, brs).

Compounds (I-34) and (I-35) shown in Table 6 were synthesized according to Example 15.

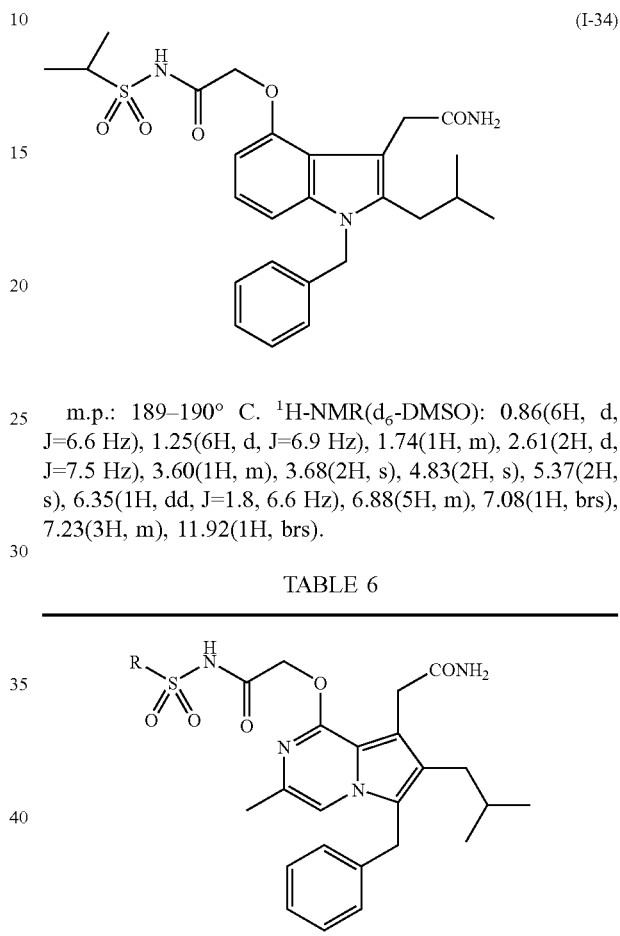

(I-34)

m.p.: 189–190° C. $^1$H-NMR(d$_6$-DMSO): 0.86(6H, d, J=6.6 Hz), 1.25(6H, d, J=6.9 Hz), 1.74(1H, m), 2.61(2H, d, J=7.5 Hz), 3.60(1H, m), 3.68(2H, s), 4.83(2H, s), 5.37(2H, s), 6.35(1H, dd, J=1.8, 6.6 Hz), 6.88(5H, m), 7.08(1H, brs), 7.23(3H, m), 11.92(1H, brs).

TABLE 6

| Compound No. | R | m.p. (° C.) | $^1$H-NMR(CDCl$_3$) |
|---|---|---|---|
| I-35 | Me | 188–190 | 0.90(6H, d, J=6.9Hz), 1.74(1H, m), 2.14(3H, s), 2.52(2H, d, J=7.2Hz), 3.32(3H, s), 3.89(2H, s), 4.21(2H, s), 5.10(2H, s), 5.57(1H, br.s), 5.75(1H, br.s), 6.95(1H, s), 6.98(2H, m), 7.28(3H, m), 10.74(1H, br). |
| I-36 | i-Pr | 162–163 | 0.89(6H, d, J=6.6Hz), 1.40(6H, d, J=6.6Hz), 1.73(1H, m), 2.13(3H, s), 2.52(2H, d, J=7.5Hz), 3.82(1H, m), 3.88(2Hs), 4.20(2H, s), 5.08(2H, s), 5.59(1H, br.s), 5.76(1H, br.s), 6.94(1H, s), 6.97(2H, m), 7.28(3H, m), 10.29(1H, br). |

Example 37

Preparation of Compound (I-37)

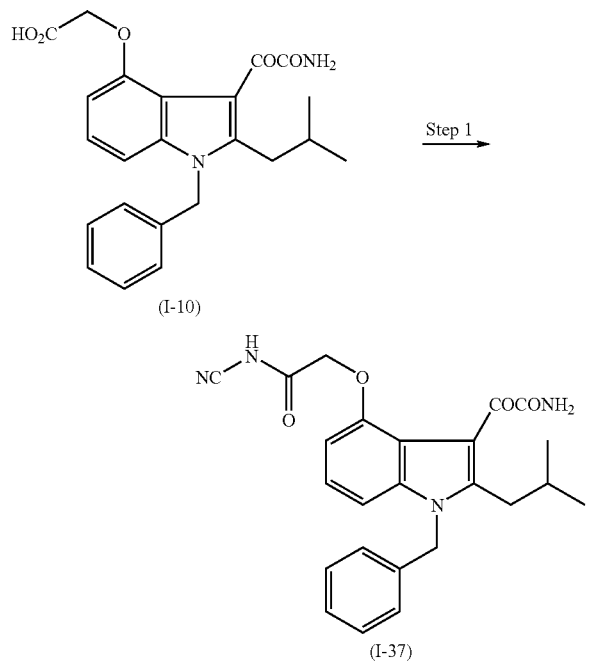

(Step 1)

To a solution of compound (I-10) (100 mg, 0.24 mg) in N,N-dimethylformamide (4 mL) was added 1,1'-carbonyl-diimidazole (48 mg, 0.30 mmol), and the reaction mixture was stirred at room temperature for 1 h. The other solution was prepared by adding 60% sodium hydride (29 mg, 0.73 mmol) to a solution of cyanamide (31 mg, 0.74 mmol) in N,N-dimethylformamide (2 mL), and stirring at room temperature for 1 h. To the reaction mixture was added dropwise the other solution, and the reaction mixture was stirred at room temperature for additional 2 h. The reaction mixture was poured into 2 mol/L hydrochloric acid and extracted with ethyl acetate. The organic layer was washed with water and brine, successively, and dried over sodium sulfate. The solvent was removed, and the residue was purified by absorbing on Sephadex LH-20 sold by Pharmacia Biotech and eluting by chloroform to give the desired compound (I-37) (94 mg, 89%) as yellow powder.

$^1$H-NMR($d_6$-DMSO): 0.88(6H, d, J=6.6 Hz), 1.87(1H, m), 2.91(2H, d, J=7.2 Hz), 4.84(2H, s), 5.54(2H, s), 6.63 (1H, t, J=4.2 Hz), 7.02(2H, m), 7.09(2H, d, J=4.2 Hz), 7.30(3H, m), 7.82(1H, brs), 8.16(1H, brs).

Compounds (I-38) and (I-39) shown in Table 7 were synthesized according to Example 37.

TABLE 7

| Compound No. | Structure | $^1$H-NMR($d_6$-DMSO) |
|---|---|---|
| I-38 | 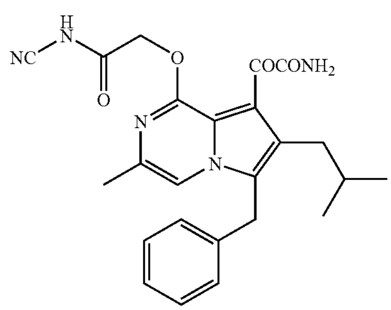 | 0.82(6H, d, J=6.6Hz), 1.74(1H, m), 2.19(3H, s), 2.68(2H, d, J=7.5Hz), 4.34(2H, s) 4.94(2H, s), 7.06–7.31(5H, m), 7.71(1H, s), 7.75(1H, br.s), 8.10(1H, br.s). |
| I-39 | 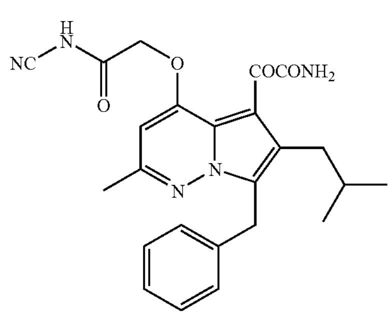 | 0.81(6H, d, J=6.3Hz), 1.76(1H, m), 2.41(3H, s), 2.66(2H, d, J=6.9Hz), 4.32(2H, s), 4.95(2H, s), 6.55(1H, s), 7.14–7.27(5H, m), 7.62(1H, br.s), 7.95(1H, br.s). |

Example 40

Preparation of Compound (I-40)

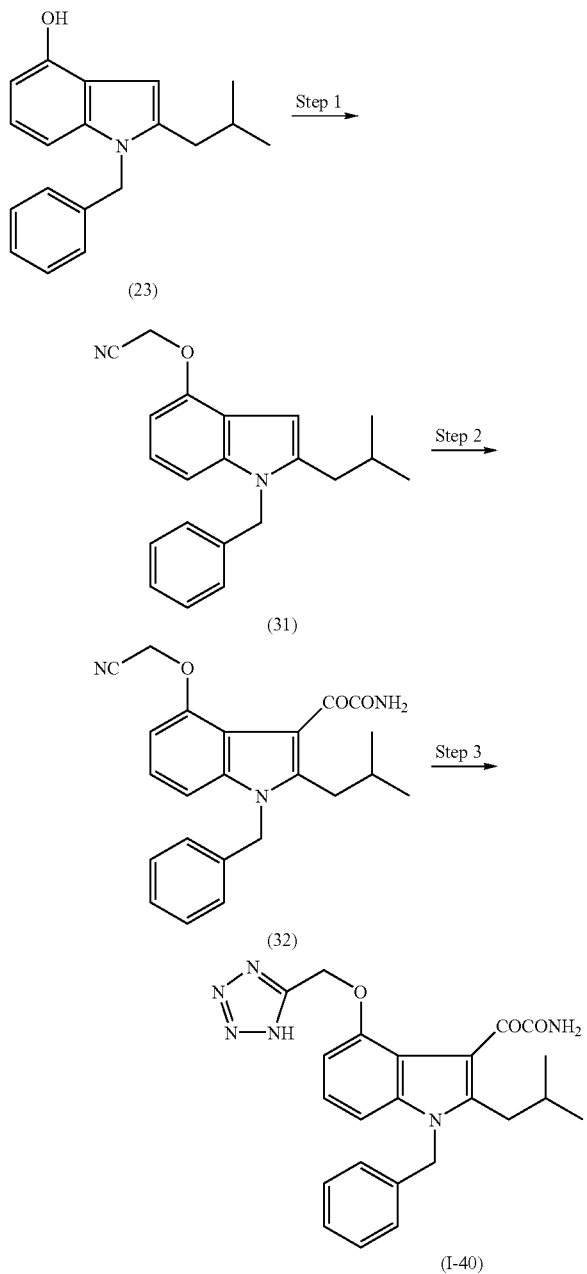

(Step 1)

Compound (23) (500 mg, 1.79 mmol) was dissolved in N,N-dimethylformaide (5 mL), and to the reaction mixture was added potassium carbonate (445 mg, 3.22 mmol), and the reaction mixture was stirred at room temperature for 30 min. To the reaction mixture were added bromoacetonitrile (150 μL, 2.15 mmol) and potassium iodide (30 mg, 0.18 mmol), and the reaction mixture was stirred for 3.5 h. The reaction mixture was diluted with water and extracted with ethyl acetate. The organic layer was washed with brine and dried over sodium sulfate. The solvent was removed, and the residue was subjected to silica gel column chromatography (ethyl acetate:hexane=85:15) to give the desired compound (31) (550 mg, 97%) as a colorless oil.

$^1$H-NMR(CDCl$_3$): 0.96(6H, d, J=6.6 Hz), 1.93(1H, m), 2.55(2H, d, J=6.9 Hz), 4.91(2H, s), 5.31(2H, s), 6.43(1H, s), 6.60(1H, d, J=8.1 Hz), 6.94(3H, m), 7.03(1H, t, J=8.1 Hz), 7.24(3H, m).

(Step 2)

To a solution of compound (31) (291 mg, 0.91 mmol) in methylene chloride was added oxalyl chloride (88 μL, 1.01 mmol), the reaction mixture was stirred at room temperature for 1 h. The reaction mixture was poured into aqueous ammonium hydroxide solution and extracted with ethyl acetate. The organic layer was washed with brine and dried over sodium sulfate. The solvent was removed, and the residue was recrystallized from ethyl acetate/hexane to give (32) (279 mg, 78%) as pale yellow crystals.

m.p.: 155–156.5° C. $^1$H-NMR(d$_6$-DMSO): 0.87(6H, d, J=6.6 Hz), 1.84(1H, m), 2.88(2H, d, J=7.2Hz), 5.12(2H, s), 5.54(2H, s), 6.84(1H, dd, J=2.1, 6.6 Hz), 7.01(2H, m), 7.13(2H, m), 7.29(3H, m), 7.42(1H, brs), 7.85(1H, brs).

(Step 3)

To a solution of compound (32) (150mg, 0.39 mg) in N,N-dimethylformamide (3 mL) were added sodium azide (38 mg, 0.58 mmol) and ammonium chloride (11 mg, 0.21 mmol), and the reaction mixture was stirred at 140° C. for 4 h. The reaction mixture was cooled, and to the reaction mixture was 2 mol/L hydrochloric acid, and the reaction mixture was extracted with ethyl acetate. The organic layer was washed with water and dried over sodium sulfate. The solvent was removed, and the residue was purified by absorbing on Sephadex LH-20 sold by Pharmacia Biotech and eluting by chloroform to give the desired compound (I-40) (138 mg, 83%) as yellow-green powder.

$^1$H-NMR(d$_6$-DMSO): 0.87(6H, d, J=6.6 Hz), 1.85(1H, m), 2.88(2H, d, J=7.5 Hz), 5.52(2H, s), 5.55(2H, s), 6.77 (1H, dd, J=3.0, 5.1 Hz), 7.05(4H, m), 7.29(3H, m), 7.48(1H, brs), 7.89(1H, brs).

Examination 1: Inhibition Test of Human Secretory Phospholipase A$_2$

Analytical Experiment

In order to identify and evaluate an inhibitor of recombinant human secretory phospholipase A$_2$, the following chromogenic assay is used. The assay herein has been applied for high volume screening with 96 well microtiterplate. A general explanation for such assay is described in "Analysis of Human Synovial Fluid Phospholipase A$_2$ on Short Chain Phosphatidylcholine-Mixed Micelles: Development of a Spectrophotometric Assay Suitable for a Microtiterplate Reader" (Analytical Biochemistry, 204, pp 190–197, 1992 by Laure. J. Reynolds. Lori L. Hughes and Edward A. Dennis:

Reagents:
Reaction Buffer
CaCl$_2$.6H$_2$O (2.19 g/L)
KCl (7.455 g/L)
Bovine Serum Albumin (fatty acid free) (1 g/L)
(Sigma A-7030)
Tris-HCl (3.94 g/L)
pH 7.5 (adjusted with NaOH)
Enzyme Buffer
0.05 M-AcONa
0.2 M-NaCl
pH 4.5 (adjusted with acetic acid)

DTNB
198 mg of 5,5'-dithiobis-2-benzoic acid (manufactured by Wako Pure Chemicals) is dissolved in 100 mL of H₂O
pH 7.5 (adjusted with NaOH)
Substrate Solution
100 mg of racemic 1,2-bis(heptanoylthio)-1,2-dideoxy-sn-glycero-3-phosphorylcholine is dissolved in 1 mL of chloroform.
Triton-X 100
624.9 mg of Triton-X 100 is dissolved in 100 mL of the reaction buffer.
Enzyme Solution
Type I enzyme: A sPLA$_2$ solution (330 ng/μL) (described in A. Kanda et. al., Biochimica et Biophysica Acta. 1171 (1992) 1–10) is used in the assay (enzyme solution 27 μL is diluted with 1973 μL of the reaction buffer).
Type II enzyme: 1 mg of sPLA$_2$ is dissolved in 1 mL of an enzyme buffer. Thereafter, the solution is maintained at 4° C. In the assay, 6 μL of the solution is diluted with 1994 μL of the reaction buffer.
Type V and type X enzymes: cDNA sequences encoding human type V and type X sPLA2 (Chen et., al., J. Biol. Chem., 1994. 269, 2365–2368 and Cupillard et., al., J. Biol. Chem., 1997, 272, 15745–15752) were inserted forwardly into downstream of promoter of pSVL SV40 Late Promoter Expression Vector (Amersham Pharmacia Biotech K. K.), mammalian cell expression vector. The recombinant expression vectors were transfected into CHO host cells by LipofectAMINE regent (Gibco BRL.) according to the attached manual and the cells expressed each of human type V and type X sPLA2 stably. After each expressing cells were cultured in σ-MEM medium including 10% fetal serum albumin for 3 days, the cells supernatant were collected and measured enzymatic activity.

Enzyme Reaction: for 1 plate of Microtiterplate
1) 0.106 mL of the substrate solution was put in a centrifugal tube, and nitrogen gas was jetted to remove the solvent. 0.54 mL of Triton-X 100 was added thereto, the mixture was stirred, thereafter it was sonified in a bath type sonification to dissolve. To the resulting product were added 17.8 mL of the reaction buffer and 0.46 mL of DTNB, and 0.18 mL each of the admixture is poured to a 96 well microtiterplate.
2) 10 μL of a test compound (or solvent blank) was added in accordance with alignment of previously set plates.
3) Incubation was conducted at 40° C. for 15 minutes.
4) 90 ng/well in case of human type I enzyme, 50 ng/well in case of human type II enzyme, 40 μL/well in case of human type V enzyme, and 15 μL/well in case of human type X enzyme were reacted.
5) Changes in absorbancy for 30 minutes for humane type I, type II, and type X enzyme and for 45 min for human type V enzyme, were measured by a plate reader, and inhibition activity was calculated (OD: 405 nm).
6) IC$_{50}$ was determined by plotting log concentration with respect to inhibition values within 10% to 90% inhibiting range.

The result of sPLA$_2$ inhibition examination is shown in Table 8.

TABLE 8

| Compound No. | IC$_{50}$ (μM) | | | |
|---|---|---|---|---|
| | type I | type II | type V | type X |
| I-1 | >0.7 | >1.0 | >1.0 | 0.032 |
| I-2 | >0.7 | >1.0 | >1.0 | 0.043 |
| I-3 | >0.7 | >1.0 | >1.0 | 0.048 |
| I-9 | >0.7 | >1.0 | >1.0 | 0.022 |
| I-10 | >0.7 | >1.0 | >1.0 | 0.013 |
| I-11 | >0.7 | >1.0 | >1.0 | 0.012 |
| I-12 | >0.7 | >1.0 | >1.0 | 0.032 |
| I-13 | >0.7 | >1.0 | >1.0 | 0.028 |
| I-15 | >0.7 | >1.0 | >1.0 | 0.037 |
| I-21 | >0.7 | >1.0 | >1.0 | 0.008 |
| I-22 | >0.7 | >1.0 | >1.0 | 0.008 |
| I-23 | >0.7 | >1.0 | >1.0 | 0.006 |
| I-24 | >0.7 | >1.0 | >1.0 | 0.023 |
| I-25 | >0.7 | >1.0 | >1.0 | 0.007 |
| I-32 | >0.7 | >1.0 | >1.0 | 0.046 |

Examination 2: Immunohistochemical Analysis in Human Colon Cancer Tissues with Type X Anti-sPLA$_2$ Antibody.

In this experiment, anti-human type X sPLA$_2$ antibody that was described in The Journal of Biological Chemistry Vol. 274, No. 48, pp. 34203–34211 was used. Paraffin embedded preparations of human colon cancer tissues and corresponding normal tissues were purchased from Biochain Inc. (San Leandro, Calif.). The tissue sections in the slides were dewaxed, treated in methanol containing 0.3% H$_2$O$_2$ for 30 min to remove the endogenous peroxidase activity and incubated with 5% normal goat serum for 20 min. The slides were then incubated with type X anti-sPLA$_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% H$_2$O$_2$ for 10 min resulting in the appearance of color dependent on the peroxidase activity to visualize the type X sPLA$_2$ expression in the tissue preparations. In addition, the nuclei were counterstained with 0.4% hematoxylin solution. Positive signals representative for type X sPLA$_2$ expression was visualized as a dark-brownish color of diaminobenzidine deposit. The neutralization of type X sPLA$_2$ specific signals was conducted by incubating type X anti-sPLA$_2$ antibody with purified type X sPLA$_2$ protein (60 μg/mL) for 2 hr before the addition to the slides.

Consequently, positive signals representative for type X sPLA$_2$ expression were not obviously detected in normal colon, but strongly detected in the tumor cells in human colon adenocarcinoma tissues. Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human colorectal cancer tissues.

Examination 3: Immunohistochemical Analysis in Human Lung Cancer Tissues with Type X Anti-sPLA$_2$ Antibody.

In this experiment, anti-human type X sPLA$_2$ antibody which was described in The Journal of Biological Chemistry Vol. 274, No. 48, pp. 34203–34211 was used. Paraffin embedded preparations of human lung cancer tissues and corresponding normal tissues were purchased from Biochain Inc. (San Leandro, Calif.). The tissue sections in the slides were dewaxed, treated in methanol containing 0.3% $H_2O_2$ for 30 min to remove the endogenous peroxidase activity and incubated with 5% normal goat serum for 20 min. The slides were then incubated with type X anti-sPLA$_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% $H_2O_2$ for 10 min resulting in the appearance of color dependent on the peroxidase activity to visualize the type X sPLA$_2$ expression in the tissue preparations. In addition, the nuclei were counterstained with 0.4% hematoxylin solution. Positive signals representative for type X sPLA$_2$ expression was visualized as a dark-brownish color of diaminobenzidine deposit. The neutralization of type X sPLA$_2$ specific signals was conducted by incubating type X anti-sPLA$_2$ antibody with purified type X sPLA$_2$ protein (60 μg/mL) for 2 hr before the addition to the slides.

Consequently, positive signals representative for type X sPLA$_2$ expression were weakly observed in type II pneumocytes in normal human lung. In contrast, the positive signals were strongly detected in tumor cells in the lung tissues prepared from patients of lung cancer. Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human lung cancer tissues.

Examination 4: Immunohistochemical Analysis in Human Liver Cancer Tissues with Type X Anti-sPLA$_2$ Antibody.

In this experiment, anti-human type X sPLA$_2$ antibody which was described in The Journal of Biological Chemistry Vol. 274, No. 48, pp. 34203–34211 was used. Paraffin embedded preparations of human liver cancer tissues and corresponding normal tissues were purchased from Biochain Inc. (San Leandro, Calif.). The tissue sections in the slides were dewaxed, treated in methanol containing 0.3% $H_2O_2$ for 30 min to remove the endogenous peroxidase activity and incubated with 5% normal goat serum for 20 min. The slides were then incubated with type X anti-sPLA$_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% $H_2O_2$ for 10 min resulting in the appearance of color dependent on the peroxidase activity to visualize the type X sPLAX expression in the tissue preparations. In addition, the nuclei were counterstained with 0.4% hematoxylin solution. Positive signals representative for type X sPLA$_2$ expression was visualized as a dark-brownish color of diaminobenzidine deposit. The neutralization of type X sPLA$_2$ specific signals was conducted by incubating type X anti-sPLA$_2$ antibody with purified type X sPLA$_2$ protein (60 μg/mL) for 2 hr before the addition to the slides.

Consequently, positive signals representative for type X sPLA$_2$ expression were weakly observed in hepatic lobule and Kupffer's satellate cells in normal human liver. In contrast, the positive signals were strongly detected in tumor cells in the liver tissues prepared from patients of liver cancer. Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human liver cancer tissues.

Examination 5: Immunohistochemical Analysis in Human Stomach Cancer Tissues with Type X Anti-sPLA$_2$ Antibody.

In this experiment, anti-human type X sPLA$_2$ antibody which was described in The Journal of Biological Chemistry Vol. 274, No. 48, pp. 34203–34211 was used. Paraffin embedded preparations of human stomach cancer tissues and corresponding normal tissues were purchased from Biochain Inc. (San Leandro, Calif.). The tissue sections in the slides were dewaxed, treated in methanol containing 0.3% $H_2O_2$ for 30 min to remove the endogenous peroxidase activity and incubated with 5% normal goat serum for 20 min. The slides were then incubated with type X anti-sPLA$_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% $H_2O_2$ for 10 min resulting in the appearance of color dependent on the peroxidase activity to visualize the type X sPLA$_2$ expression in the tissue preparations. In addition, the nuclei were counterstained with 0.4% hematoxylin solution. Positive signals representative for type X sPLA$_2$ expression was visualized as a dark-brownish color of diaminobenzidine deposit. The neutralization of type X sPLA$_2$ specific signals was conducted by incubating type X anti-sPLA$_2$ antibody with purified type X sPLA$_2$ protein (60 μg/mL) for 2 hr before the addition to the slides.

Consequently, positive signals representative for type X sPLA$_2$ expression were not obviously detected in normal stomach, but strongly detected in tumor cells in the stomach tissues prepared from patients of stomach cancer. Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human stomach cancer tissues.

Examination 6: Immunohistochemical Analysis in Human Renal Cancer Tissues with Type X Anti-sPLA$_2$ Antibody.

In this experiment, anti-human type X sPLA$_2$ antibody which was described in The Journal of Biological Chemistry Vol. 274, No. 48, pp. 34203–34211 was used. Paraffin embedded preparations of human renal cancer tissues and corresponding normal tissues were purchased from Biochain Inc. (San Leandro, Calif.). The tissue sections in the slides were dewaxed, treated in methanol containing 0.3% $H_2O_2$ for 30 min to remove the endogenous peroxidase activity and incubated with 5% normal goat serum for 20 min. The slides were then incubated with type X anti-sPLA$_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% $H_2O_2$ for 10 min resulting in the appearance of color dependent on the peroxidase activity to visualize the type X $sPLA_2$ expression in the tissue preparations. In addition, the nuclei were counterstained with 0.4% hematoxylin solution. Positive signals representative for type X $sPLA_2$ expression was visualized as a dark-brownish color of diaminobenzidine deposit. The neutralization of type X $sPLA_2$ specific signals was conducted by incubating type X anti-$sPLA_2$ antibody with purified type X $sPLA_2$ protein (60 μg/mL) for 2 hr before the addition to the slides.

Consequently, positive signals representative for type X $sPLA_2$ expression were weakly observed in glomerular mesangial cells in normal kidney. In contrast, the positive signals were strongly detected in tumor cells in the kidney prepared from patients of renal cancer. Since the addition of type X $sPLA_2$ protein resulted in abolishment of the signals, they were verified as the specific signals for type X $sPLA_2$. In addition, there was no positive signal when IgG prepared from non-immunized rabbit was used. Taken together, these findings suggest that the expression of type X $sPLA_2$ protein was greatly elevated in human renal cancer tissues.

Examination 7: Immunohistochemical Analysis in Human Gallbladder Cancer Tissues with Type X anti-$sPLA_2$ antibody.

In this experiment, anti-human type X $sPLA_2$ antibody which was described in The Journal of Biological Chemistry Vol. 274, No. 48, pp. 34203–34211 was used. Paraffin embedded preparations of human gallbladder cancer tissues and corresponding normal tissues were purchased from Biochain Inc. (San Leandro, Calif.). The tissue sections in the slides were dewaxed, treated in methanol containing 0.3% $H_2O_2$ for 30 min to remove the endogenous peroxidase activity and incubated with 5% normal goat serum for 20 min. The slides were then incubated with type X anti-$sPLA_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% $H_2O_2$ for 10 min resulting in the appearance of color dependent on the peroxidase activity to visualize the $sPLA_2$-X expression in the tissue preparations. In addition, the nuclei were counterstained with 0.4% hematoxylin solution. Positive signals representative for type X $sPLA_2$ expression was visualized as a dark-brownish color of diaminobenzidine deposit. The neutralization of type X $sPLA_2$ specific signals was conducted by incubating type X anti-$sPLA_2$ antibody with purified type X $sPLA_2$ protein (60 μg/mL) for 2 hr before the addition to the slides.

Consequently, positive signals representative for type X $sPLA_2$ expression were not obviously detected in normal gallbladder tissues, but strongly detected in tumor cells in the gallbladder tissues prepared from patients of gallbladder cancer. Since the addition of type X $sPLA_2$ protein resulted in abolishment of the signals, they were verified as the specific signals for type X $sPLA_2$. In addition, there was no positive signal when IgG prepared from non-immunized rabbit was used. Taken together, these findings suggest that the expression of type X $sPLA_2$ protein was greatly elevated in human gallbladder cancer tissues.

Examination 8: Immunohistochemical Analysis in Human Prostate Cancer Tissues with Type X Anti-$sPLA_2$ Antibody.

In this experiment, anti-human type X $sPLA_2$ antibody which was described in The Journal of Biological Chemistry Vol. 274, No. 48, pp. 34203–34211 was used. Paraffin embedded preparations of human prostate cancer tissues and corresponding normal tissues were purchased from Biochain Inc. (San Leandro, Calif.). The tissue sections in the slides were dewaxed, treated in methanol containing 0.3% $H_2O_2$ for 30 min to remove the endogenous peroxidase activity and incubated with 5% normal goat serum for 20 min. The slides were then incubated with type X anti-$sPLA_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% $H_2O_2$ for 10 min resulting in the appearance of color dependent on the peroxidase activity to visualize the type X $sPLA_2$ expression in the tissue preparations. In addition, the nuclei were counterstained with 0.4% hematoxylin solution. Positive signals representative for type X $sPLA_2$ expression was visualized as a dark-brownish color of diaminobenzidine deposit. The neutralization of type X $sPLA_2$ specific signals was conducted by incubating type X anti-$sPLA_2$ antibody with purified type X $sPLA_2$ protein (60 μg/mL) for 2 hr before the addition to the slides.

Consequently, positive signals representative for type X $sPLA_2$ expression were not obviously detected in normal prostates, but strongly detected in tumor cells in the prostate tissues prepared from patients of prostate cancer. Since the addition of type X $sPLA_2$ protein resulted in abolishment of the signals, they were verified as the specific signals for type X $sPLA_2$. In addition, there was no positive signal when IgG prepared from non-immunized rabbit was used. Taken together, these findings suggest that the expression of type X $sPLA_2$ protein was greatly elevated in human prostate cancer tissues.

Examination 9: Immunohistochemical Analysis in Human Pancreatic Cancer Tissues with Type X Anti-$sPLA_2$ Antibody.

In this experiment, anti-human type X $sPLA_2$ antibody which was described in The Journal of Biological Chemistry Vol. 274, No. 48, pp. 34203–34211 was used. Paraffin embedded preparations of human pancreatic cancer tissues and corresponding normal tissues were purchased from Biochain Inc. (San Leandro, Calif.). The tissue sections in the slides were dewaxed, treated in methanol containing 0.3% $H_2O_2$ for 30 min to remove the endogenous peroxidase activity and incubated with 5% normal goat serum for 20 min. The slides were then incubated with type X anti-$sPLA_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% $H_2O_2$ for 10 min resulting in the appearance of color dependent on the peroxidase activity to visualize the type X sPLA$_2$ expression in the tissue preparations. In addition, the nuclei were counterstained with 0.4% hematoxylin solution. Positive signals representative for type X sPLA$_2$ expression was visualized as a dark-brownish color of diaminobenzidine deposit. The neutralization of type X sPLA$_2$ specific signals was conducted by incubating type X anti-sPLA$_2$ antibody with purified sPLA$_2$-X protein (60 µg/mL) for 2 hr before the addition to the slides.

Consequently, positive signals representative for type X sPLA$_2$ expression were not obviously detected in normal pancreas, but strongly detected in tumor cells in the pancreas prepared from patients of pancreatic cancer. Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human pancreatic cancer tissues.

Examination 10: Immunohistochemical Analysis in Human Testis Cancer Tissues with Type X Anti-sPLA$_2$ Antibody.

In this experiment, anti-human type X sPLA$_2$ antibody which was described in The Journal of Biological Chemistry Vol. 274, No. 48, pp. 34203–34211 was used. Paraffin embedded preparations of human testis cancer tissues and corresponding normal tissues were purchased from Biochain Inc. (San Leandro, Calif.). The tissue sections in the slides were dewaxed, treated in methanol containing 0.3% H$_2$O$_2$ for 30 min to remove the endogenous peroxidase activity and incubated with 5% normal goat serum for 20 min. The slides were then incubated with type X anti-sPLA$_2$ antibody (6 µg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 µg/mL diaminobenzidine hydrochloride substrate dissolved in 50 mmol/L Tris-HCl (pH 7.6) containing 0.006% H$_2$O$_2$ for 10 min resulting in the appearance of color dependent on the peroxidase activity to visualize the type X sPLA$_2$ expression in the tissue preparations. In addition, the nuclei were counterstained with 1% methyl green dye in 0.1 mol/L sodium acetate (pH 4.0). Positive signals representative for type X sPLA$_2$ expression was visualized as a dark-brownish color of diaminobenzidine deposit. The neutralization of type X sPLA$_2$ specific signals was conducted by incubating type X anti-sPLA$_2$ antibody with purified type X sPLA$_2$ protein (60 µg/mL) for 2 hr before the addition to the slides.

Consequently, positive signals representative for type X sPLA$_2$ expression were weakly observed in some parts of the seminiferous tubles of normal testis. In contrast, the positive signals were strongly detected in malignant cells present in the seminiferous tubles and/or the epithelium of seminal vesicles in the testis prepared from patients of testis cancer. Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human testis cancer tissues.

Examination 11: Immunohistochemical Analysis in Human Ovarian Cancer Tissues with Type X Anti-sPLA$_2$ Antibody.

In this experiment, anti-human type X sPLA$_2$ antibody which was described in The Journal of Biological Chemistry Vol. 274, No. 48, pp. 34203–34211 was used. Paraffin embedded preparations of human ovarian cancer tissues and corresponding normal tissues were purchased from Biochain Inc. (San Leandro, Calif.). The tissue sections in the slides were dewaxed, treated in methanol containing 0.3% H$_2$O$_2$ for 30 min to remove the endogenous peroxidase activity and incubated with 5% normal goat serum for 20 min. The slides were then incubated with type X anti-sPLA$_2$ antibody (6 µg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 µg/mL diaminobenzidine hydrochloride substrate dissolved in 50 mmol/L Tris-HCl (pH 7.6) containing 0.006% H$_2$O$_2$ for 10 min resulting in the appearance of color dependent on the peroxidase activity to visualize the type X sPLA$_2$ expression in the tissue preparations. In addition, the nuclei were counterstained with 1% methyl green dye in 0.1 mol/L sodium acetate (pH 4.0). Positive signals representative for type X sPLA$_2$ expression was visualized as a dark-brownish color of diaminobenzidine deposit. The neutralization of type X sPLA$_2$ specific signals was conducted by incubating type X anti-sPLA$_2$ antibody with purified type X sPLA$_2$ protein (60 µg/mL) for 2 hr before the addition to the slides.

Consequently, positive signals representative for type X sPLA$_2$ expression were not obviously detected in normal ovary, but strongly detected in the malignant cells present in the epithelium of ovarian follicles and/or oviducts in the ovary prepared from patients of ovarian cancer. Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human ovarian cancer tissues.

Examination 12: Immunohistochemical Analysis in Human Ovarian Cancer Tissues with Type X Anti-sPLA$_2$ Antibody.

In this experiment, anti-human type X sPLA$_2$ antibody which was described in The Journal of Biological Chemistry Vol. 274, No. 48, pp. 34203–34211 was used. Paraffin embedded preparations of human ovarian cancer tissues (malignant melanoma) and corresponding normal tissues were purchased from Biochain Inc. (San Leandro, Calif.). The tissue sections in the slides were dewaxed, treated in methanol containing 0.3% H$_2$O$_2$ for 30 min to remove the endogenous peroxidase activity and incubated with 5% normal goat serum for 20 min. The slides were then incubated with type X anti-sPLA$_2$ antibody (6 µg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 µg/mL diaminobenzidine hydrochloride substrate dissolved in 50 mmol/L Tris-HCl (pH 7.6) containing 0.006% H$_2$O$_2$ for 10 min resulting in the appearance of color dependent on the peroxidase activity to visualize the type X sPLA$_2$ expression in the tissue preparations. In addition, the nuclei were counterstained with 1% methyl green dye in 0.1 mol/L sodium acetate (pH 4.0). Positive signals representative for type X sPLA$_2$ expression was visualized as a dark-brownish color of diaminobenzidine deposit. The neutralization of type X sPLA$_2$ specific signals was conducted by incubating anti-type X sPLA$_2$ antibody with purified sPLA$_2$-X protein (60 μg/mL) for 2 hr before the addition to the slides.

Consequently, positive signals representative for type X sPLA$_2$ expression were weakly observed in the melanocytes of stratum spinosum and/or stratum basale in skin epidermis in normal human skin. In contrast, the positive signals were strongly detected in hypertrophied melanocytes in the skin prepared from patients of skin cancer (malignant melanoma). Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human ovatian cancer (malignant melanoma) tissues.

Examination 13: Immunohistochemical Analysis in Human Cerebrum of Brain Tissues with Type X Anti-sPLA$_2$ Antibody.

In this experiment, anti-human type X sPLA$_2$ antibody which was described in The Journal of Biological Chemistry Vol. 274, No. 48, pp. 34203–34211 was used. Paraffin embedded preparations of human Alzheimer's disease brain cerebrum tissues and corresponding normal tissues were purchased from Biochain Inc. (San Leandro, Calif.). The tissue sections in the slides were dewaxed, treated in methanol containing 0.3% H$_2$O$_2$ for 30 min to remove the endogenous peroxidase activity and incubated with 5% normal goat serum for 20 min. The slides were then incubated with type X anti-sPLA$_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% H$_2$O$_2$ for 10 min resulting in the appearance of color dependent on the peroxidase activity to visualize the type X sPLA$_2$ expression in the tissue preparations. In addition, the nuclei were counterstained with Gill's 0.4% hematoxylin solution. Positive signals representative for type X sPLA$_2$ expression was visualized as a dark-brownish color of diaminobenzidine deposit. The neutralization of type X sPLA$_2$ specific signals was conducted by incubating type X anti-sPLA$_2$ antibody with purified type X sPLA$_2$ protein (60 μg/mL) for 2 hr before the addition to the slides.

Consequently, positive signals representative for type X sPLA$_2$ expression were not obviously detected in normal brain cerebrum tissues, but strongly detected in some neuronal regions, especially in senile plaque and neurofibrillary tangle regions, in the cerebrum tissues prepared from patients of Alzheimer's disease. Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human Alzheimer's disease brain tissues.

Examination 14: Immunohistochemical Analysis in Human Liver Cirrhosis Tissues with Type X Anti-sPLA$_2$ Antibody.

In this experiment, anti-human type X sPLA$_2$ antibody which was described in The Journal of Biological Chemistry Vol. 274, No. 48, pp. 34203–34211 was used. Paraffin embedded preparations of human liver cirrhosis tissues and corresponding normal tissues were purchased from Biochain Inc. (San Leandro, Calif.). The tissue sections in the slides were dewaxed, treated in methanol containing 0.3% H$_2$O$_2$ for 30 min to remove the endogenous peroxidase activity and incubated with 5% normal goat serum for 20 min. The slides were then incubated with type X anti-sPLA$_2$ antibody (6 μg/mL) in PBS containing 0.1% bovine serum albumin for 14 hr at 4° C. After washing with PBS, they were incubated with biotin-conjugated goat anti-rabbit IgG antibody for 30 min followed by treatment with peroxidase avidin-biotin complex reagent (Vector Laboratories). After washing, the samples were processed with 200 μg/mL diaminobenzidine hydrochloride substrate dissolved in 50 mmol/L Tris-HCl (pH 7.6) containing 0.006% H$_2$O$_2$ for 10 min resulting in the appearance of color dependent on the peroxidase activity to visualize the type X sPLA$_2$ expression in the tissue preparations. In addition, the nuclei were counterstained with 0.4% hematoxylin solution. Positive signals representative for type X sPLA$_2$ expression was visualized as a dark-brownish color of diaminobenzidine deposit. The neutralization of type X sPLA$_2$ specific signals was conducted by incubating type X anti-sPLA$_2$ antibody with purified type X sPLA$_2$ protein (60 μg/mL) for 2 hr before the addition to the slides.

Consequently, positive signals representative for type X sPLA$_2$ expression were weakly observed in hepatic lobule and Kupffer's satellite cells in normal human liver tissues. In contrast, the positive signals were strongly detected in the hepatocytes of psudolobules in the liver prepared from patients of liver cirrhosis. Since the addition of type X sPLA$_2$ protein resulted in abolishment of the signals, they were verified as the specific signals for type X sPLA$_2$. In addition, there was no positive signal when IgG prepared from non-immunized rabbit was used. Taken together, these findings suggest that the expression of type X sPLA$_2$ protein was greatly elevated in human liver cirrhosis tissues.

Examination 15: Effects of sPLA$_2$ Inhibitors on Human Type X sPLA$_2$-Induced Oleic Acid Release in Human Colon Calcinoma Cell Lines, HT-29 Cells.

Human colon calcinoma cell lines, HT-29 cells (obtained from ATCC) were cultured in DMEM supplemented with 10% fetal calf serum. The cells were washed by phosphate-buffered saline (PBS), detached from culture plates by treatment with trypsin/EDTA solution and further washed by PBS. The resulting cells were resuspended in Hanks' buffered saline containing 0.1% bovine serum albumin (BSA) at a density of 12.5×10$^6$ cells/mL. Aliquots of the cell suspension (0.4 ml) were transferred into polypropylene tubes and test compounds dissolved in DMSO solution (final concentration; 10 μM) were added. After preincubation for 10 min at 37° C., 100 nM purified human type X sPLA$_2$ enzyme (Hanasaki et al J. Biol. Chem. (1999) 274, 34203–34211) was added (final volume of 0.5 mL). After incubation for 30 min at 37° C., the reaction was stopped by the addition of 2 ml Dole's reagent (heptane:2-propanol:1M H$_2$SO$_4$=10:40:1, v/v/v). According to the method of Tojo et al. (J. lipid Res. (1993) 34, 837–844), the released fatty acids were extracted, labeled with 9-anthryldiazomethane (Funakoshi Co.), and the oleic acid was quantified by reverse-phase high performance chromatography (LiChroCART 125-4 Superspher 100 RP-18 column (Merck). From each data, the value in the absence of type X sPLA$_2$ was subtracted. The amount of released oleic acid in the presence of each test compound was expressed as the percentage of the increased content by the addition of type X sPLA$_2$ enzyme. As shown in FIG. 9, each test compound significantly inhibited the type X sPLA$_2$-induced oleic acid release.

Examination 16: Effects of sPLA$_2$ Inhibitors on Type X sPLA$_2$-Induced PGE$_2$ Production in Human Colon Carcinoma Cell Lines, HT-29 Cells.

HT-29 cells were seeded into 24-well plates at a density of 2.5×10$^5$ cells/well. After incubation for 24 h, the cells were washed three times with PBS and incubated with 30 ng/mL of recombinant human tumor necrosis factor-α (R&D Systems, Inc.) in DMEM medium supplemented with 10% fetal bovine serum for 18 h at 37° C. After washing with PBS, the cells were preincubated with or without test compounds (at a final concentration of 10 μM; dissolved in DMSO) in Hanks' buffered saline containing 0.1% BSA for 10 min at 37° C., and then stimulated with 100 nM purified human type X sPLA$_2$ enzyme in a final volume of 0.5 mL. After incubation for 3 h at 37° C, the culture supernatant was collected following the centrifugation for the removal of floating cells, and its PGE$_2$ content was quantified with an enzyme-immunoassay kit (Cayman Chemicals Co.). From each data, the value in the absence of type X sPLA$_2$ was subtracted. The amount of PGE$_2$ in the presence of each test compound was expressed as the percentage of the PGE$_2$ content produced by the addition of type X sPLA$_2$ enzyme. As shown in Table 9, each test compound significantly blocked the type X sPLA$_2$-induced PGE$_2$ production.

Potential involvement of PGE$_2$ in the progression of tumors has been described in Cancer Research 59, 5093–5096, 1999. Since the compounds in the present invention significantly block the type X sPLA$_2$-induced PGE$_2$ production, they can be applied as antitumor agents.

TABLE 9

| Compoud (10 μM) | Oleic acid release | PGE2 production |
|---|---|---|
| No treatment group | 100 ± 2.8 | 100 ± 22.7 |
| I-4 | 13.8 ± 1.8** | 35.3 ± 40.2* |
| I-10 | −0.2 ± 5.7** | −12.7 ± 7.9** |
| I-21 | 11.8 ± 0.6** | −6.6 ± 7.1** |
| I-23 | −2.0 ± 5.1** | 9.0 ± 28.1** |

Student's t-test (*P < 0.05, **P < 0.01)

Examination 17: Effects of sPLA$_2$ Inhibitors on Type X sPLA$_2$-Induced Fatty Acid Release From Isolated Human Lipoproteins.

LDL was isolated from human plasma by sequential ultracentrifugation method (Havel et al. J. Clin. Invest. 34,1345–1353 (1955)). LDL (0.5 mg/mL) was incubated with 10 nmol/L of human type X sPLA$_2$ in the assay mixture containing 12.5 mmol/L Tris-HCl buffer (pH 8.0), 125 mg/L bovine serum albumin and 1 mmol/L calcium chloride for 4 hr at 37° C. Fatty acids released from lipoprotein were extracted by Dole's method (Dole et al. J. Biol. Chem. 235, 2595–2599 (1960)), labeled with 9-anthryldiazomethane according to a known method (Hanasaki et al., J. Biol. Chem. 274, 34203–34211 (1999)) and measured by detecting the fluorescence of labeled fatty acids using reverse-phase high performance chromatography (LiChroCART 125-4 Superspher 100 RP-18 column (Merck). For the inhibition assay of drugs, sPLA$_2$ inhibitors (final concentration of 10 μM) were added at almost the same time as the addition of sPLA$_2$ into the reaction solution. The results are presented in Table 10.

TABLE 10

| Compound | % of Inhibition (10 μM) |
|---|---|
| I-10 | 91.27 |
| I-22 | 91.72 |
| I-30 | 97.46 |

Since the compounds in the present invention significantly block the type X sPLA$_2$-induced fatty acid release from human lipoproteins, they can be applied as antiatherogenic drugs.

Formulation Example

It is to be noted that the following Formulation Examples 1 to 9 are mere illustration, but not intended to limit the scope of the invention. The term "active ingredient" means the compounds represented by the formula (I), the prodrugs thereof, their pharmaceutical acceptable salts, or their solvates.

Formulation Example 1

Hard gelatin capsules are prepared using of the following ingredients:

|  | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
|---|---|
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

| Tablets, each containing 60 mg of active ingredient, are made as follows. | |
|---|---|
| Active ingredient | 60 mg |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

| Capsules, each containing 80 mg of active ingredient, are made as follows: | |
|---|---|
| Active ingredient | 80 mg |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

| Suppository, each containing 225 mg of active ingredient, are made as follows: | |
|---|---|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

| Suspensions, each containing 50 mg of active ingredient per 5 ml dose, are made as follows: | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

| An intravenous formulation may be prepared as follows: | |
|---|---|
| Active ingredient | 100 mg |
| Isotonic saline | 1000 mL |

The solution of the above ingredients generally is administered intravenously to a subject at a rate of 1 mL per minute.

Industrial Applicability

It is provided that compounds represented by the general formula (I) in the present invention, exhibit a type X sPLA$_2$ inhibitory effect and are useful as a preventing agent or treating agent for cancer, liver cirrhosis, Alzheimer's disease and/or arteriosclerosis.

The invention claimed is:

1. A compound of the general formula (VI):

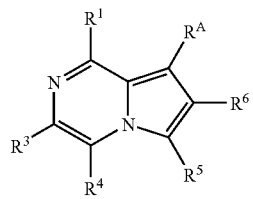

(VI)

wherein R$^1$ is —(L$^1$)-(acidic group) wherein L$^1$ is a group represented by the formula:

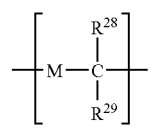

wherein M is —CH$_2$—, —O—, —N(R$^{30}$)—, or —S—; R$^{28}$ and R$^{29}$ are each independently hydrogen atom, C1–C10 alkyl, aryl, aralkyl, carboxy, or halogen, or a group represented by the formula:

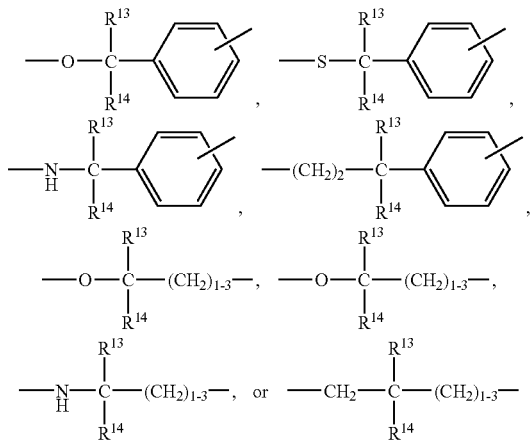

wherein $R^{13}$ and $R^{14}$ are each independently hydrogen atom, C1–C10 alkyl, C1–C10 aralkyl, carboxy, alkyloxycarbonyl, or halogen;

$R^3$ and $R^4$ are each independently selected from hydrogen atom, (h) C1–C10 alkyl, C2–C6 alkenyl, C2–C6 alkynyl, C7–C12 aralkyl, C7–C12 alkaryl, C3–C8 cycloalkyl, phenyl, tolyl, xylyl, biphenylyl, C1–C10 alkyloxy, C1–C6 alkyloxy C1–C6 alkyl, C1–C6 alkyloxy C1–C6 alkyloxy, C1–C6 alkylcarbonyl, C1–C6 alkylcarbonylamino, C1–C6 alkyloxyamino, C1–C6 alkyloxyaminocarbonyl, mono or di C1–C6 alkylamino, C1–C10 alkylthio, C1–C6 alkylthiocarbonyl, C1–C6 alkylsulfinyl, C1–C6 alkylsulfonyl, C2–C6 haloalkyloxy, C1–C6 haloalkylsulfonyl, C1–C10 haloalkyl, C1–C6 hydroxyalkyl, C1–C6 alkyloxycarbonyl, —(CH$_2$)$_{1-8}$—O—(C1–C6 alkyl), benzyloxy, aryloxy, arylthio, —(CONHSO$_2$R$^{39}$) wherein R$^{39}$ is C1–C6 alkyl or aryl, —CHO, amino, amidino, halogen, carbamyl, carboxyl, carbalkoxy, —(CH$_2$)$_{1-8}$—COOH, cyano, cyanoguanidino, guanidino, hydrazide, hydrazino, hydroxy, hydroxyamino, nitro, phosphono, —SO$_3$H, thioacetal, thiocarbonyl, a carbocyclic group, a heterocyclic group or (j) a carbocyclic or heterocyclic group substituted with a group defined in (h);

$R^5$ is (f) C1–C20 alkyl, C2–C20 alkenyl, C2–C20 alkynyl, a carbocyclic group, or a heterocyclic group or (g) a group defined in (f) each substituted independently with at least one group selected from C1–C10 alkyl, C2–C6 alkenyl, C2–C6 alkynyl, C7–C12 aralkyl, C7–C12 alkaryl, C3–C8 cycloalkyl, phenyl, tolyl, xylyl, biphenylyl, C1–C10 alkyloxy, C1–C6 alkyloxy C1–C6 alkyl, C1–C6 alkyloxy C1–C6 alkyloxy, C1–C6 alkylcarbonyl, C1–C6 alkylcarbonylamino, C1–C6 alkyloxyamino, C1–C6 alkyloxyaminocarbonyl, mono or di C1–C6 alkylamino, C1–C10 alkylthio, C1–C6 alkylthiocarbonyl, C1–C6 alkylsulfinyl, C1–C6 alkylsulfonyl, C2–C6 haloalkyloxy, C1–C6 haloalkylsulfonyl, C1–C10 haloalkyl, C1–C6 hydroxyalkyl, C1–C6 alkyloxycarbonyl, —(CH$_2$)$_{1-8}$—O—(C1–C6 alkyl), benzyloxy, aryloxy, arylthio, —(CONHSO$_2$R$^{40}$) wherein R$^{40}$ is C1–C6 alkyl or aryl, —CHO, amino, amidino, halogen, carbamyl, carboxyl, carbalkoxy, —(CH$_2$)$_{1-8}$—COOH, cyano, cyanoguanidino, guanidino, hydrazide, hydrazino, hydroxy, hydroxyamino, nitro, phosphono, —SO$_3$H, thioacetal, thiocarbonyl, a carbocyclic group or a heterocyclic group;

$R^6$ is optionally substituted C4–C8 alkyl, C3–C8 cycloalkyl C1–C4 alkyl, or aryl C1–C4 alkyl;

$R^4$ is represented by the formula:

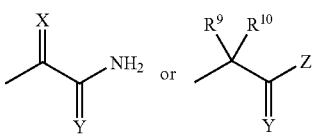

wherein $R^9$ and $R^{10}$ are each independently hydrogen atom, C1–C3 alkyl, or halogen;
X and Y are each independently oxygen atom or sulfur atom; and
Z is —NH$_2$ or —NHNH$_2$;
a C1–C6 alkyl, acyloxyalkyl, or alkyloxycarbonyloxyalkyl ester thereof, or a pharmaceutically acceptable salt thereof.

2. The compound of claim 1, wherein $R^1$ is —(L$^3$)—R$^{11}$ wherein L$^3$ is —OCH$_2$—, —SCH$_2$—, —NH—CH$_2$—, —CH$_2$CH$_2$—, —O—CH(CH$_3$)—, or —O—CH(CH$_2$CH$_2$C$_6$H$_5$)—, and
$R^{11}$ is represented by the formula:

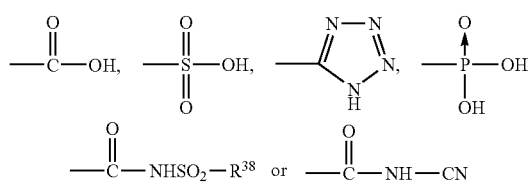

wherein $R^{38}$ is C1–C6 alkyl, C1–C3 haloalkyl, or aryl optionally substituted with C1–C6 alkyl, halogen, optionally substituted amino or nitro;
a C1–C6 alkyl, acyloxyalkyl, or alkyloxycarbonyloxyalkyl ester thereof, or a pharmaceutically acceptable salt thereof.

3. The compound of claim 1, wherein $R^3$ is hydrogen atom, C1–C6 alkyl, C3–C6 cycloalkyl, aryl, or a heterocyclic group, and $R^4$ is hydrogen atom or halogen;
a C1–C6 alkyl, acyloxyalkyl, or alkyloxycarbonyloxyalkyl ester thereof, or a pharmaceutically acceptable salt thereof.

4. The compound of claim 1, wherein $R^5$ is —(CH$^2$)$_{1-6}$—R$^{15}$ wherein $R^{15}$ is represented by the formula:

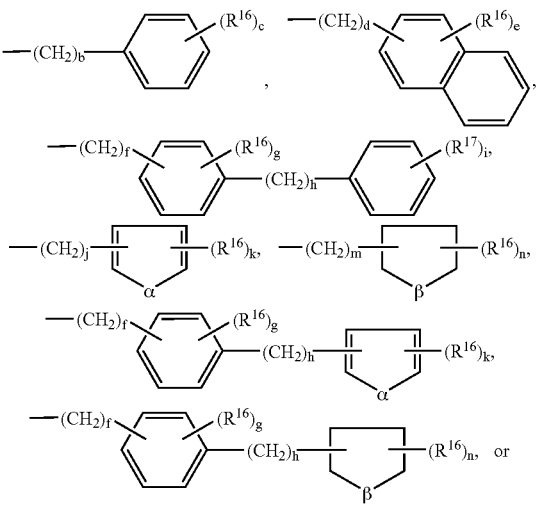

-continued

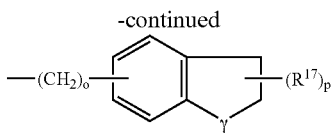

wherein b, d, f, h, j, m, and o are each independently an integer from 0 to 2, $R^{16}$ and $R^{17}$ are each independently halogen, C1–C10 alkyl, C1–C10 alkyloxy, C1–C10 alkylthio, aryloxy, or C1–C10 haloalkyl, α is oxygen atom or sulfur atom, β is —CH$_2$— or —(CH$_2$)$_2$—, γ is oxygen atom or sulfur atom, c, i, and p are each independently an integer from 0 to 5, e is an integer from 0 to 7, g is an integer from 0 to 4, k and n are each independently an integer from 0 to 3;

a C1–C6 alkyl, acyloxyalkyl, or alkyloxycarbonyloxyalkyl ester thereof, or a pharmaceutically acceptable salt thereof.

5. The compound of claim 4, wherein $R^5$ is —CH$_2$—$R^{18}$ wherein $R^{18}$ is represented by the formula:

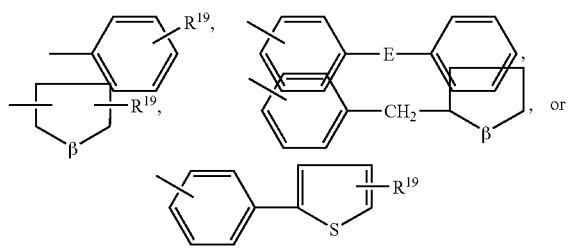

wherein β is —CH$_2$—, or (CH$_2$)$_2$—; $R^{19}$ is hydrogen atom, C1–C3 alkyl or halogen; and E is a bond, —CH$_2$—, or —O—;

a C1–C6 alkyl, acyloxyalkyl, or alkyloxycarbonyloxyalkyl ester thereof, or a pharmaceutically acceptable salt thereof.

6. The compound of claim 1, wherein $R^1$ is —OCH$_2$COOH or —OCH$_2$CONHSO$_2$R$^{38}$ wherein $R^{38}$ is C1–C6 alkyl, C1 haloalkyl, or aryl;

a C1–C6 alkyl, acyloxyalkyl, or alkyloxycarbonyloxyalkyl ester thereof, or a pharmaceutically acceptable salt thereof.

7. The compound of claim 1, wherein $R^6$ is C4–C6 alkyl;

a C1–C6 alkyl, acyloxyalkyl, or alkyloxycarbonyloxyalkyl ester thereof, or a pharmaceutically acceptable salt thereof.

8. The compound of claim 1, wherein $R^4$ is —CH$_2$CONH$_2$ or —COCONH$_2$;

a C1–C6 alkyl, acyloxyalkyl, or alkyloxycarbonyloxyalkyl ester thereof, or a pharmaceutically acceptable salt thereof.

9. A compound of the general formula (III):

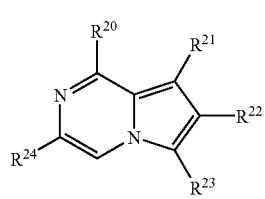

(III)

wherein $R^{20}$ is —OCH$_2$COOH, —OCH$_2$CONHSO$_2$CH$_3$, or —OCH$_2$CONHSO$_2$C$_6$H$_5$; $R^{21}$ is —COCONH$_2$, —CH$_2$CONH$_2$, or —CH$_2$CONHNH$_2$; $R^{22}$ is C4–C6 alkyl; $R^{23}$ is —CH$_2$—$R^{18}$ wherein $R^{18}$ represented by the formula:

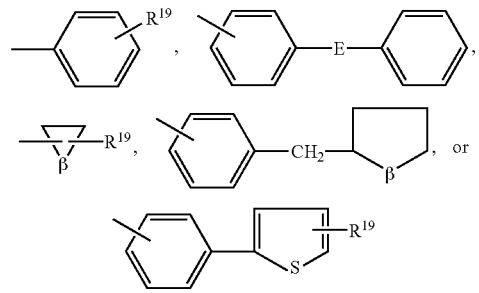

wherein β is —(CH$_2$)$_{1-6}$—; $R^{19}$ is hydrogen, C1–C3 alkyl, or halogen; E is a single bond, —CH$_2$—, or —O—; $R^{24}$ is hydrogen or C1–C6 alkyl;

a C1–C6 alkyl, acyloxyalkyl, or alkyloxycarbonyloxyalkyl ester thereof, or a pharmaceutically acceptable salt thereof.

10. A pharmaceutical composition which comprises the compound of any one of claims 1 or 9 together with a pharmaceutically acceptable carrier or diluent.

11. An method for inhibiting type X sPLA$_2$ enzyme, which comprises contacting type X sPLA$_2$ enzyme protein with an effective amount of the compound of any one of claims 1 or 9.

12. A method for preparing a pharmaceutical composition, which comprises mixing the compound of any one of claims 1 or 9 with a pharmaceutically acceptable carrier or diluent.

13. The compound of claim 1, wherein $R^1$ is —OCH$_2$COOH, —OCH$_2$CONHCN or —OCH$_2$CONHSO$_2$R$^{46}$ wherein $R^{46}$ is methyl, ethyl, propyl, isopropyl, phenyl or trifluoromethyl;

$R^3$ is methyl; $R^4$ is hydrogen atom; $R^5$ is —CH$_2$—$R^{47}$ wherein $R^{47}$ is phenyl, benzyl, cyclopentyl or cyclohexyl; $R^6$ is butyl, isobutyl, pentyl, benzyl or cyclopentylmethyl; $R^4$ is —COCONH$_2$ or —CH$_2$CONH$_2$;

a C1–C6 alkyl, acyloxyalkyl, or alkyloxycarbonyloxyalkyl ester thereof, or a pharmaceutically acceptable salt thereof.

14. The compound of claim 1, wherein $R^6$ is isobutyl;

a C1–C6 alkyl, acyloxyalkyl, or alkyloxycarbonyloxyalkyl ester thereof, or a pharmaceutically acceptable salt thereof.

15. The compound of claim 14, wherein $R^1$ is —OCH$_2$COOH or —OCH$_2$CONHSO$_2$R$^{48}$ wherein $R^{48}$ is methyl or phenyl; $R^3$ is methyl; $R^4$ is hydrogen atom;

$R^5$ is —CH$_2$—$R^{49}$ wherein $R^{49}$ is phenyl, benzyl, cyclopentyl or cyclohexyl;

$R^4$ is —COCONH$_2$;

a C1–C6 alkyl, acyloxyalkyl, or alkyloxycarbonyloxyalkyl ester thereof, or a pharmaceutically acceptable salt thereof.

* * * * *